United States Patent
Siejko et al.

(10) Patent No.: US 10,123,742 B2
(45) Date of Patent: Nov. 13, 2018

(54) METHODS AND DEVICES COMBINING MULTIPLE CARDIAC RATE MEASUREMENTS WITH INTERVAL CORRECTION AND ARRHYTHMIA DECISION BYPASS

(71) Applicant: CARDIAC PACEMAKERS, INC., St. Paul, MN (US)

(72) Inventors: Krzysztof Z. Siejko, Maple Grove, MN (US); Venugopal Allavatam, Fremont, CA (US); Amy Jean Brisben, St. Paul, MN (US); Stephen J. Hahn, Shoreview, MN (US); Keith L. Herrmann, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 67 days.

(21) Appl. No.: 15/362,851

(22) Filed: Nov. 29, 2016

(65) Prior Publication Data
US 2017/0156669 A1   Jun. 8, 2017

Related U.S. Application Data

(60) Provisional application No. 62/262,048, filed on Dec. 2, 2015.

(51) Int. Cl.
*A61B 5/00* (2006.01)
*A61B 5/0452* (2006.01)
(Continued)

(52) U.S. Cl.
CPC ............ *A61B 5/686* (2013.01); *A61B 5/0205* (2013.01); *A61B 5/7221* (2013.01); *A61B 7/04* (2013.01); *A61N 1/39622* (2017.08); *A61B 5/021* (2013.01); *A61B 5/0245* (2013.01); *A61B 5/04017* (2013.01); *A61B 5/0422* (2013.01); *A61B 5/04525* (2013.01);
(Continued)

(58) Field of Classification Search
None
See application file for complete search history.

(56) References Cited

U.S. PATENT DOCUMENTS

| 5,480,412 | A | * | 1/1996 | Mouchawar | ....... | A61N 1/36542 607/116 |
| 6,721,597 | B1 | | 4/2004 | Bardy et al. | | |

(Continued)

*Primary Examiner* — Brian T Gedeon
(74) *Attorney, Agent, or Firm* — Seager, Tufte & Wickhem LLP

(57) ABSTRACT

In some examples, cardiac cycle detection may be used as an approach to cardiac activity tracking, with one or more second approaches to cardiac activity tracking also available for use. Additional rate measurement relying on different sources or analyses may require extra power consumption over the cycle detection methods. Therefore, new methods and devices are disclosed that selectively activate a second cardiac rate measurement. In some illustrative methods and devices, decisions are made as to whether and which previously collected data, if any, is to be discarded, replaced, or corrected upon activation of the second cardiac rate measurement. In some illustrative methods and devices, a cardiac cycle detection approach to cardiac activity tracking may be bypassed by a second cardiac rate measurement.

16 Claims, 14 Drawing Sheets

(51) Int. Cl.

| | | |
|---|---|---|
| *A61B 5/021* | (2006.01) | |
| *A61B 5/11* | (2006.01) | |
| *A61N 1/39* | (2006.01) | |
| *A61N 1/365* | (2006.01) | |
| *A61B 7/04* | (2006.01) | |
| *A61B 5/0205* | (2006.01) | |
| *A61B 5/04* | (2006.01) | |
| *A61B 5/1455* | (2006.01) | |
| *A61B 5/042* | (2006.01) | |
| *A61B 5/0245* | (2006.01) | |

(52) U.S. Cl.
CPC ......... *A61B 5/1102* (2013.01); *A61B 5/14552* (2013.01); *A61N 1/36585* (2013.01); *A61N 1/3987* (2013.01)

(56) References Cited

U.S. PATENT DOCUMENTS

| | | | |
|---|---|---|---|
| 6,754,528 B2 | 6/2004 | Bardy et al. | |
| 7,248,921 B2 | 7/2007 | Palreddy et al. | |
| 7,330,757 B2 | 2/2008 | Ostroff et al. | |
| 8,116,867 B2 | 2/2012 | Ostroff | |
| 8,160,686 B2 | 4/2012 | Allavatam et al. | |
| 8,160,687 B2 | 4/2012 | Warren et al. | |
| 8,160,697 B2 | 4/2012 | Warren et al. | |
| 8,185,198 B2* | 5/2012 | Palreddy ............ | A61B 5/04525 607/5 |
| 8,346,357 B2* | 1/2013 | Palreddy ............ | A61B 5/04525 607/5 |
| 8,409,107 B2 | 4/2013 | Sweeney et al. | |
| 8,521,276 B2 | 8/2013 | Sweeney et al. | |
| 8,565,878 B2 | 10/2013 | Allavatam et al. | |
| 8,712,523 B2 | 4/2014 | Sanghera et al. | |
| 8,831,711 B2 | 9/2014 | Freer et al. | |
| 9,149,637 B2 | 10/2015 | Warren et al. | |
| 9,179,853 B2* | 11/2015 | Sanghera ........... | A61N 1/36592 |
| 9,451,892 B2 | 9/2016 | Siejko | |
| 9,451,893 B2 | 9/2016 | Siejko et al. | |
| 9,629,565 B2 | 4/2017 | Siejko | |
| 9,895,071 B2* | 2/2018 | Siejko ................. | A61B 5/0245 |
| 2015/0196758 A1 | 7/2015 | Stahmann et al. | |
| 2017/0112399 A1 | 4/2017 | Brisben et al. | |
| 2017/0113040 A1 | 4/2017 | Brisben et al. | |
| 2017/0113050 A1 | 4/2017 | Brisben et al. | |
| 2017/0113053 A1 | 4/2017 | Brisben et al. | |
| 2017/0156617 A1 | 6/2017 | Allavatam et al. | |

\* cited by examiner

METHODS AND DEVICES COMBINING MULTIPLE CARDIAC RATE MEASUREMENTS WITH INTERVAL CORRECTION AND ARRHYTHMIA DECISION BYPASS

CROSS REFERENCE TO RELATED APPLICATIONS

The present application claims the benefit of and priority to U.S. Provisional Patent Application Ser. No. 62/262,048, filed Dec. 2, 2015, and titled METHODS AND DEVICES COMBINING MULTIPLE CARDIAC RATE MEASUREMENTS WITH INTERVAL CORRECTION AND ARRHYTHMIA DECISION BYPASS, the disclosure of which is incorporated herein by reference.

BACKGROUND

Many existing implantable or wearable cardiac rhythm management products, such as monitoring devices, pacing devices, and/or defibrillators, rely on the detection of individual cardiac cycles or "beats" in a cardiac electrical signal, such as the cardiac electrogram, surface electrocardiogram (ECG), and/or the subcutaneous ECG, to obtain a measurement of the rate of cardiac activity. Cardiac cycle detection is not the only available manner of obtaining a cardiac rate from the cardiac electrical signal, and other data sources may also provide cardiac rate measures.

For devices having plural cardiac rates available for use, new and alternative approaches to managing rate measurements from plural methodologies are desired.

OVERVIEW

The present inventors have recognized, among other things, that continuous improvement is allowing devices to move beyond merely using cardiac cycle detection to track cardiac activity. New and different methods of integrating additional cardiac activity sources are desired.

In some examples, cardiac cycle detection may be used as a default approach to cardiac activity tracking. Additional rate measurement relying on different sources or analysis may require extra power consumption over the cycle detection methods. Therefore, new methods and devices are disclosed that selectively activate a second cardiac rate measurement when needed. In some illustrative methods and devices, decisions are made as to whether and which previously collected data, if any, is to be discarded, replaced, or corrected upon activation of the second cardiac rate measurement.

This overview is intended to briefly introduce the subject matter of the present patent application, and is not intended to provide an exclusive or exhaustive explanation of the invention. The detailed description is included to provide further information.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
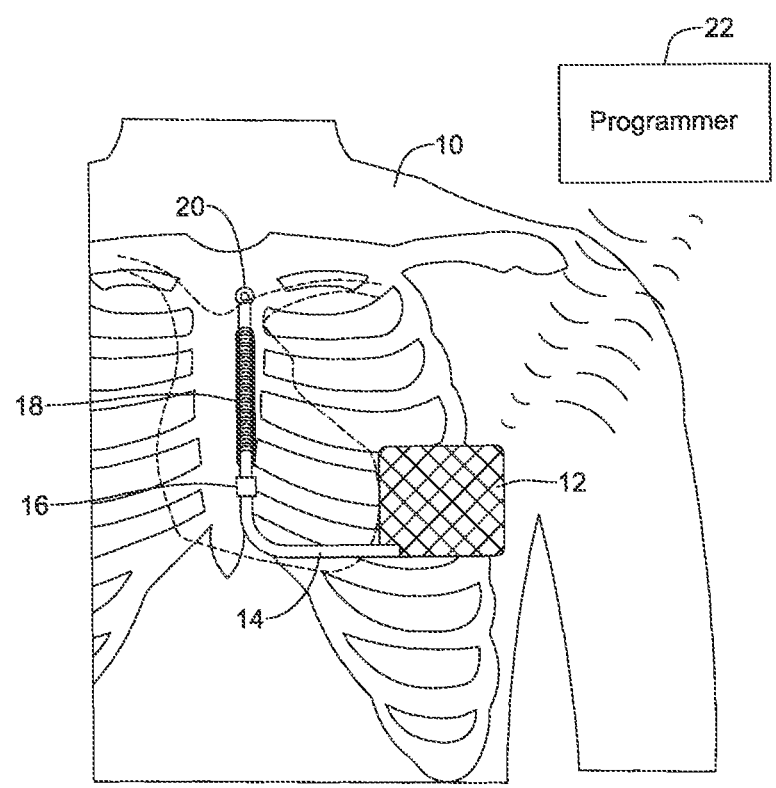
FIG. 1 shows an illustrative implantable cardiac rhythm management system.

FIG. 1 shows the S-ICD System™ from Cameron Health, Inc., and Boston Scientific Corporation, as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may include componentry appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12.

In some examples, the present invention may be implemented in a system as shown in FIG. 1. In other examples, an implantable or wearable cardiac monitor may have multiple electrodes on a housing and/or lead to define two or more sensing vectors. Leadless devices, such as leadless cardiac pacemakers for implantation inside the heart, may have multiple sensing electrodes on or extending from a canister or housing to define multiple sensing vectors. Wearable defibrillators or pacemakers may also provide multiple cutaneous electrodes on the anterior and/or posterior thorax of the patient, and may even include indifferent electrodes elsewhere such as on a limb. Transvenous and/or epicardial implantable devices may have an active housing adapted for use in sensing along with plural electrodes for sensing on one or more leads, as is well known in the art. For example, a transvenous device may have a right ventricular lead with atrial and ventricular sensing electrodes as well as an indifferent electrode on the canister. In alternative approaches, a device may include a lead placed beneath the sternum or ribcage without touching the heart, such as by inclusion of a substernal lead.

Specific to the device shown in FIG. 1, unlike prior art defibrillators and pacemakers that include electrodes in or on the heart, the device uses only far-field electrodes outside the ribcage and away from the heart for detecting cardiac activity. This can make counting cardiac cycles more difficult, as the source of the detected signal may be harder to distinguish. For example, while a ventricular depolarization detected with a transvenous, intracardiac electrode may be quite sharp and narrow in width, the same signal will be wider and less sharp when detected in the far field. In some field products, T-wave overdetection has been observed in which individual cardiac cycles are counted twice, with a detection occurring on the R-wave and again on the T-wave. While significant effort is expended to avoid and/or identify and correct such overdetection, further improvements are desirable.

Figure 4:
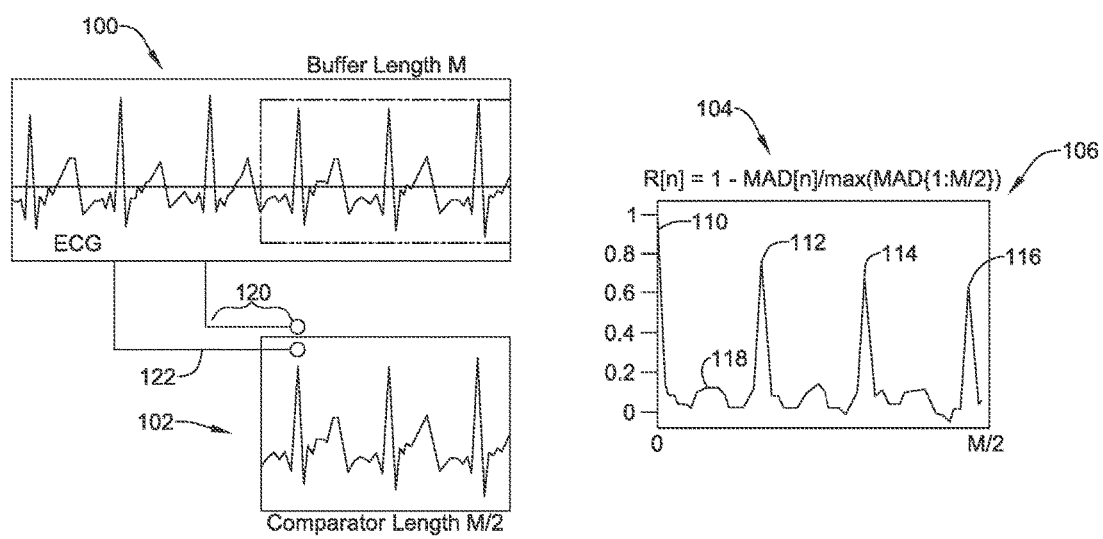
FIG. 4 shows an illustrative method of cardiac rate calculation using blocks of data, rather than detected cardiac cycles.

One approach is to use a rate relying on detecting cardiac cycles as well as a second cardiac rate measure obtained by another approach. The second cardiac rate may be obtained in various ways. Some examples may use cardiac rate measurements illustrated in copending U.S. patent application Ser. Nos. 14/819,817, 14/819,851, and 14/819,889, the disclosures of which are incorporated herein by reference (FIG. 4, below, shows a high level example). Other examples may use spectral content to determine a cardiac rate, or may reference data other devices. For example, a device as in FIG. 1 may communicate to a second implantable device, such as a monitor or leadless cardiac pacemaker implanted inside the heart, to obtain a rate therefrom. See, for example, US PG Patent Application Publication 20150196758, titled SYSTEMS AND METHODS FOR DETECTING CARDIAC ARRHYTHMIAS, the disclosure of which is incorporated herein by reference. Other examples may rely on a different data type, such as blood pressure data, pulse oximetry, cardiac motion, or heart sounds, for example, to determine or estimate cardiac rate.

Some examples focus on determining whether and when to activate a second rate calculation. Some further examples focus on determining which data to use and/or correct from the first rate calculation when the second rate calculation is operating. In any of the following examples, when a correction is made to data, an associated report may be generated or a marker placed in a stream of data to facilitate later physician review. For example, physicians often review stored episodes of cardiac data relating to occasions when therapy has been delivered, or a device has prepared to deliver therapy even if therapy is ultimately withheld. Reports showing data associated with therapy delivery or preparations may include specific markers indicating correction of data, whether for addressing overdetection by a cardiac cycle detection system, or for correcting or changing data related to whether a device has identified an arrhythmia in an X/Y counter or other analytic tool. If arrhythmia bypass takes place as in FIG. 11, for example, the point in time of start of bypass may be specifically marked on a physician report. Thus the results of analysis using a second cardiac rate that are at variance with results using a first cardiac rate or detection scheme can be presented to the physician for greater clarity and understanding.

Figure 2:
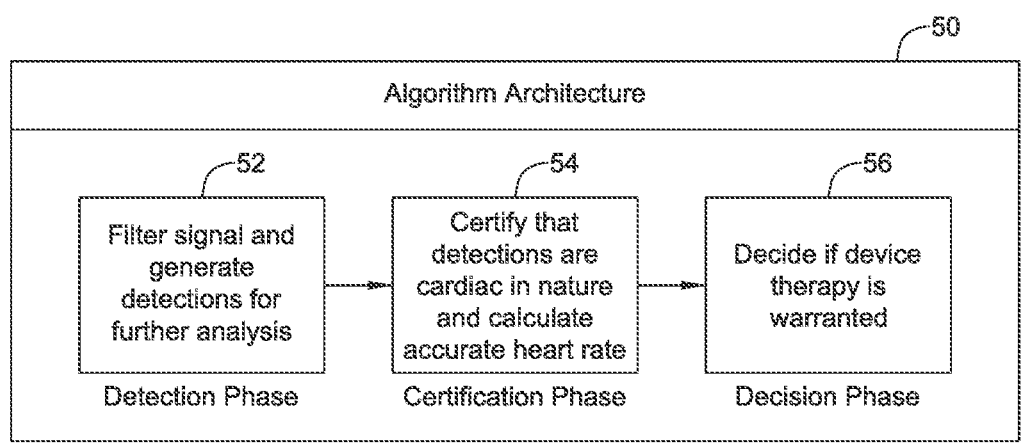
FIG. 2 shows an illustrative cardiac signal analysis architecture.

FIG. 2 shows an illustrative cardiac signal analysis architecture. The architecture 50 includes a detection phase 52 in which the input signal is filtered and cardiac cycle detections are generated for further analysis. Filtering may include both analog domain and digital domain filtering. For example a bandpass filter may be applied in the analog domain to remove DC and high frequency content, for example, using ranges of 3 to 40 Hz. Additional band stop filtering may be applied in the digital domain to remove 50/60 Hz line noise, and additional band-pass filtering may be performed to obtain desired cardiac signal bands in the range of between about 3-10 Hz and about 30-40 Hz. Other filter architectures may be used. Some examples related to filtering may be found in U.S. Provisional Patent Application 62/262,043, titled AUTOMATIC DETERMINATION AND SELECTION OF FILTERING IN A CARDIAC RHYTHM MANAGEMENT DEVICE, the disclosure of which is incorporated herein by reference.

Figure 3:
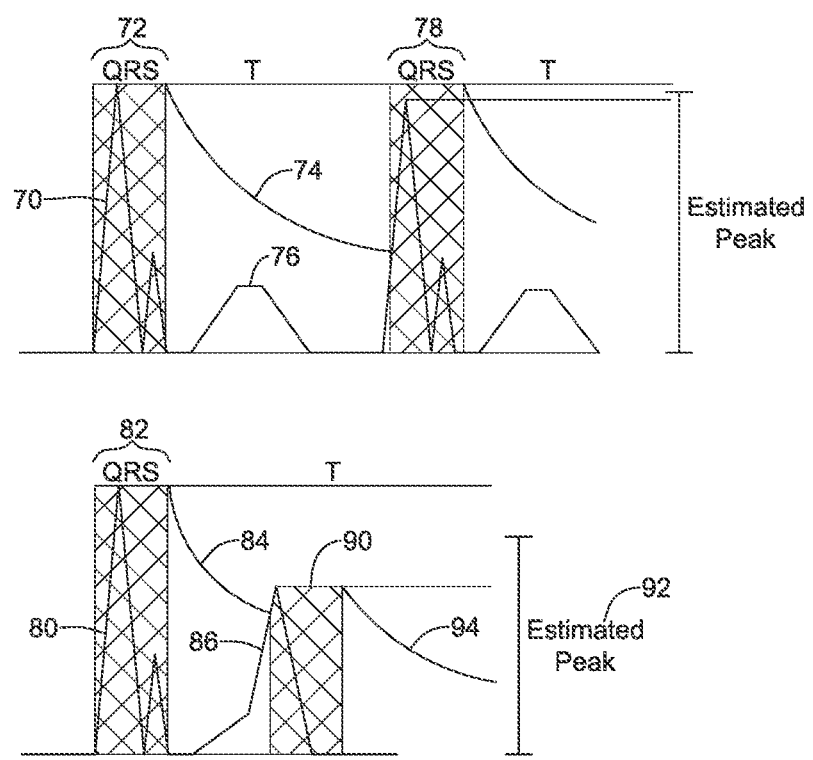
FIG. 3 shows operation of a detection profile to detect cardiac cycles using the R-wave, and shows an illustrative difficulty referred to as T-wave overdetection.

FIG. 3 shows an example of cycle detection. Some examples of cardiac cycle detection may be found, for example, in U.S. Pat. No. 8,565,878, titled ACCURATE CARDIAC EVENT DETECTION IN AN IMPLANTABLE CARDIAC STIMULUS DEVICE, the disclosure of which is incorporated herein by reference. FIG. 3 is further discussed below.

Detections generated by detection phase 52 pass to certification phase 54. Certification phase 54 may be designed to remove or correct for detections that are non-cardiac in nature, passing only those that are cardiac and not double detected for use in rate calculation. Certification may include, for example, identification and removal of cycle detections caused by noise, saturation, or wandering baseline as discussed, among other examples, in U.S. Pat. No. 7,248,921, titled METHODS AND DEVICES FOR PERFORMING CARDIAC WAVEFORM APPRAISAL, U.S. Pat. No. 8,712,523, titled IMPLANTABLE DEFIBRILLATOR SYSTEMS AND METHODS WITH MITIGATIONS FOR SATURATION AVOIDANCE AND ACCOMMODATION, and U.S. Pat. No. 8,831,711, titled IMPLANTABLE CARDIAC SYSTEMS WITH BASELINE CORRECTION IN RESPONSE TO NOISE DETECTION, the disclosures of which are incorporated herein by reference.

Certification phase 54 may also remove overdetections using, for example, methods and devices shown in U.S. Pat. Nos. 8,160,686 and/or 8,160,687, both titled METHODS AND DEVICES FOR ACCURATELY CLASSIFYING CARDIAC ACTIVITY, the disclosures of which are incorporated herein by reference. Certification phase 54 may also use methods (for transvenous systems in particular) to identify and eliminate far-field detection where only near field detection is desired. Certification phase 54 may be omitted in some examples.

Cardiac rate may be calculated using by measuring the intervals between individual detections that have been certified as cardiac and correct. A set of 1 to 8 intervals may be averaged to obtain an average cycle length, which can then be mathematically converted to a rate. For example, a 4RR average may be the average of the previous four intervals between certified R-wave detections, and may be used to determine cardiac rate, where a 4RR average of 500 milliseconds would equal to 120 beats per minute (BPM).

Decision phase 56 operates to decide whether device therapy is warranted, for those devices that can deliver therapy. Decision phase 56 may rely on detected cardiac rate along, or a combination of cardiac rate and other factors such as factors related to cardiac signal shape using, for example, R-waves, QRS complex, or other parts of the cardiac electrical signal, or non-cardiac electrical signals such as heart sounds, blood pressure measurements, patient activity or posture, etc. Some examples of decision phase may have a tiered approach in which, if the cardiac rate is below a tachycardia threshold, therapy is withheld, while if cardiac rate is above a ventricular fibrillation threshold, therapy delivery is considered necessary, while rates between the tachycardia threshold and ventricular fibrillation threshold warrant further analysis using, for example, static or dynamic template matching, width, or other factors.

A common approach, referenced below in several places, is for the decision phase to itself have two parts. A first decision is made as to whether a particular iteration of the architecture's operation indicates a treatable condition. This decision is tied to each cardiac cycle detection, or to only those detections that pass certification phase 54. A set of first decisions is retained in a counting filter, for example, an X/Y filter or a number-of-intervals-to-detect (NID) filter. As used herein, the phase "X/Y filter" should be understood to include both NID and X/Y filter approaches.

An X/Y filter, for example, tracks how many iterations of the decision phase 56 come to the conclusion that a treatable condition may exists (X) of a preceding set of iterations (Y). Typical thresholds for X/Y may be 8/12, 18/24, 30/40, for example. Various analysis and manipulations may be used for an X/Y filter. For example, in an analysis using a 4RR average, explained above, once the 4RR average exceeds a fast rate threshold, the X/Y filter may go from 0/Y to 1/Y, in a conservative method. Alternatively, for a 4RR average, the first time the rate goes above the fast rate threshold, the X/Y filter may jump 4/Y, in an aggressive method, where the use of the larger seeding is based on the knowledge that it took several fast cardiac cycle detections to get the 4RR average over the threshold. Other manipulations may, for example, reduce the X/Y filter by steps of 1 to 3 if a cardiac cycle detection from the detection phase 52 fails at certification 54 due to noise and/or overdetection analysis. As the X/Y filter operates, new analysis outcomes go into and out of the filter data in a first in-first out manner.

The second stage or tier of analysis in the decision phase 56 may look at the overall rhythm using the X/Y filter output. For example, a threshold for treatable condition declaration may take place at an X/Y filter level of 18/24. Some examples may further apply rules for persistence, for example as described in U.S. Pat. No. 8,160,697, titled METHOD FOR ADAPTING CHARGE INITIATION FOR AN IMPLANTABLE CARDIOVERTER-DEFIBRILLATOR, the disclosure of which is incorporated herein by reference, to require that the treatable overall rhythm remain in place for one or several consecutive cycle detections.

Other examples for decision phase 56 methods/devices may be bound in U.S. Pat. No. 7,330,757, titled METHOD FOR DISCRIMINATING BETWEEN VENTRICULAR AND SUPRAVENTRICULAR ARRHYTHMIAS, in which both rate and morphology analysis may be used in a tiered fashion. For example, a ventricular tachycardia (VT) rate zone may be defined as well as a ventricular fibrillation (VF) rate zone, with the boundary for VF at a higher rate than VT. When the calculated rate is in the VT zone, morphology analysis, such as the matching of detected cardiac cycles to a template, or to each other, or assessment of the individual cycles using a metric such as width, is applied. In an example, VT zone cycles having poor template correlation relative to a normal sinus rhythm (NSR) template, and which are wide or are inconsistent in shape, may be deemed treatable; those which match the NSR and/or which are narrow and match one another may be deemed non-treatable. Continuing the example, when the rate is found to be in the VF zone, each detected cycle associated with such a rate would be found treatable.

Additional analysis may be performed using methods shown in U.S. Pat. No. 9,149,637, titled ADAPTIVE CONFIRMATION OF TREATABLE ARRHYTHMIA IN IMPLANTABLE CARDIAC STIMULUS DEVICES, the disclosures of which are incorporated herein by reference. These methods may manipulate the thresholds used in the decision phase upon completion of preparation for therapy delivery such as, for example, in a defibrillator system where several seconds may pass while a therapy delivery energy is generated by charging one or several capacitors to desired voltage/energy level.

If all the applicable rules are met, then therapy delivery will be deemed appropriate. Therapy delivery may include anti-tachycardia pacing, defibrillation or cardioversion therapy, a command to a separate device to deliver therapy, or delivery of a therapeutic substance, in various examples. For high power therapy such as defibrillation, there may be a need to continue operating the architecture 50 while therapy preparations are made, such as charging a high-power capacitor; the noted U.S. Pat. Nos. 8,160,697 and 9,149,637 describe certain illustrative methods. For non-therapy devices, such as monitoring systems, the outcomes at decision phase 56 may be used to activate data recording or storage for later retrieval, or to activate a patient alarm or alert, or to telemeter data related to unusual or elevated rate conditions to a second device/system.

FIG. 3 shows use of a detection profile to detect cardiac cycles using the R-wave as a detection target. The example also shows T-wave overdetection. A cardiac electrical signal is shown at 70; the example is based on a subcutaneous electrocardiogram, though signal 70 could as well be a cutaneously captured signal instead.

A first cardiac cycle detection is shown at 72, corresponding to the QRS complex of a patient's cardiac cycle. The shaded region is a "refractory" period in which no further detected cycles are declared to allow the QRS complex to finish prior to enabling new detections to occur. A time decaying detection threshold is depicted at 74, and starts at a level defined by prior detected cycle amplitude(s). The threshold 74 decays over time until the cardiac signal 70 crosses the detection threshold 74, generating another cardiac cycle detection at 78, again a QRS complex. The overall shape of the threshold 74 may be defined according to a "detection profile", as further detailed throughout U.S. Pat. No. 8,565,878, for example. Signal 70 has a relatively small T-wave 76, at least in proportion to the QRS complex height 72, 78, making accurate detection of cardiac cycles relatively simple.

A second signal is shown at 80. Here, again, a QRS complex is detected at 82 with corresponding refractory period, followed by the application of the detection threshold at 84. This time, however, the T-wave at 86 is larger relative to the QRS complex 82, causing a second cycle detection to occur at 90. The result is malsensing of the signal 80, with two cardiac cycle detections at 82, 90 for a single cardiac cycle having the P-Q-R-S-T waves therein. Malsensing of this sort can be perpetuated by the calculation of the estimated peak 92 of the cardiac cycle detections 82, 90. For example, the estimated peak 92 would typically be used to control the overall height of the detection thresholds 74, 84, using parameters provided by the detection profile. Further discussion of this type of T-wave overdetection is provided in U.S. Pat. No. 8,565,878, including some mitigations.

Even with various mitigations in place, overdetection of cardiac cycles based on oversensing of the cardiac signal (or non-cardiac signals) occurs in implantable and wearable therapy systems, causing unnecessary and inappropriate charging and/or therapy delivery. In monitoring systems, overdetection/oversensing can create unnecessary alerts and may fill data recorders with unhelpful data demonstrating malsensing rather than sought after intermittent cardiac impairments. For these and other reasons, additional efforts have been made to identify cardiac rate by other analyses.

FIG. 4 shows an illustrative method of cardiac rate calculation using blocks of data, rather than detected cardiac cycles. The drawing and following discussion provides a high level overview of several methods that may be used for generating a second cardiac rate estimate; additional details may be found in copending U.S. patent application Ser. Nos. 14/819,817, 14/819,851, and 14/819,889, the disclosures of which are incorporated herein by reference.

The example shows a cardiac electrical signal at 100, stored in a buffer of length M. The buffer length may be, for example, from about one to about ten seconds, with four seconds serving in several illustrative embodiments. About one half of the buffer has been extracted as a "comparator", shown at 102. The comparator 102 may be shorter than one-half the buffer length in other examples.

The comparator 102 is repeatedly compared using, for example, correlation waveform analysis or difference of area subtraction, for example (or other comparative technique) to a segment of equal length from the buffer 100. Each comparison occurs at a lag depth that begins at zero, and increases until the comparator 102 has been drawn across the buffer 100 to a desired extent. For example, supposing the buffer 100 contained 512 samples of data (four seconds at 128 Hz), and the comparator contained 256 samples of data (two seconds at 128 Hz), then the comparator could be subtracted at lag depths from 0 to 256, to yield 256 data points as shown below at 106, where each data point is calculated according to the formula shown at 104. The set of data points is referred to as R[n], with n indicating the lag depth. As seen at 106, a first peak appears at the lag depth of 0—at this point, the comparator 102 is actually compared to itself, yielding a perfect match valued at 1.0 in the chart 106.

As the lag depth increases, the match decreases quickly from the initial perfect match. As the lag depth continues to increase, a peak appears at 112. This peak corresponds to a lag depth illustrated at 120, in which the R-wave peaks in the comparator 102 each line up to R-wave peaks in the buffer 100. As the calculation occurs to the larger lag depths, a set of peaks emerges as shown at 112, 114, 116, with each peak appearing at a lag depth where the ECG signal peaks 100 line up with respective peaks in the comparator 102.

The next step is to determine which of the peaks in the graph 106 provides a best estimate of cardiac rate. An illustrative rule set would first throw out the peak at 110, as it is an artifact of the comparison at Lag=0. Next, peak 118 may be ruled out as being too short, using as an example a requirement that R[n] (formula 104) exceed a threshold that can be set in the range of about 0.3 to about 0.5 for peaks to be considered. Finally peak 112 may be selected at the peak with the shortest lag time that exceeds the height threshold. Peak 112 may be confirmed as a high confidence estimate by determining whether one or more of peak 114 and 116 are an integer multiples of the lag depth of peak 112. These integer multiple peaks 114 and 116 are referred to as "Pickets" in copending U.S. patent application Ser. Nos. 14/819,817, 14/819,851, and 14/819,889, which provide numerous additional examples and detailed discussions.

The lag depth can be converted to a cardiac rate if the sampling rate is known. For example, a lag depth of 64 samples, at 128 hertz, gives a period of 500 milliseconds and converts to 120 beats per minute. In the example shown, if the data is obtained at 128 Hz, and peak 112 is at a lag depth of about n=85, the corresponding period would be 664 milliseconds (85 times 7.8 milliseconds), converting to a rate of 90 BPM. It may be noted, for confirmation of this summary explanation, that the four second buffer 100 has six sharp R-wave peaks in it, corresponding to 90 BPM.

At least two features should be noted with respect to FIG. 4. First, rather than finding individual cardiac cycles, the method identifies lag depths of greatest similarity of the comparator 102 to the ECG 100. Therefore the outcomes are likely to be independent of an analysis that uses individual cycle detection. Second, there are measures of confidence that can be gleaned from the graph at 106—one measure is a very high peak (R[n] of 0.6 or above, for example) which will suggest a very high match between comparator 102 and buffer 100 at some lag depth, and an accurate lag depth from which rate may be calculated. Another confidence measure is the presence of pickets at integer multiples of the selected peak—here, peak 112 would be at a lag depth of about n=85, and peaks 114 and 116 would be at lag depths of about n=170 and n=255, respectively.

The method illustrated in FIG. 4 may be repeated at intervals, for example, at intervals of 500 milliseconds to 10 seconds, or more or less, as desired. If the rate found in successive iterations is similar, this also adds to confidence in the outcome.

Thus there are at least three measures of confidence in the method of FIG. 4:
Peak height
The existence of "pickets"—additional peaks at integer multiples of the lag depth of a peak
Repeated similar outcomes Rate estimates can thus be graded according to confidence, from high confidence if two or three of these factors (or other factors) are present, to low confidence if only one of the factors is present. Confidence may be used in determining which of multiple rate measurements to rely upon in making therapy decisions and at other places in the following methods, as described below.

The method illustrated in FIG. 4 is one method of calculating a cardiac rate without identifying cardiac cycles—that is, without partitioning an input signal into individual component cycles or beats using, for example, a beat/cycle detector to identify R-waves or QRS complexes. Other cardiac rate analyses may be used such as a spectral analysis in which a predominant frequency may be obtained.

It can also be observed that the rate calculation shown in FIG. 4 requires a large number of computational steps—such as the repeated subtractions of blocks of data used to generate the function R[n]. Many patients with active implantable cardiac devices spend most of their days and nights experiencing normal sinus rhythm at benign rates in the range of 50 to 100 bpm. Intensive rate calculation is not necessary during these times and could cause unnecessarily short battery life for such devices (assuming non-rechargeable batteries), or may necessitate inconvenient and frequent recharging sessions (if rechargeable batteries are used). Therefore several illustrative devices and methods below are directed toward decision processes that can turn on the more computationally intensive rate calculation only when needed.

The example in FIG. 4 illustrates a calculation performed on a fairly good cardiac signal, with consistent waveform shapes generally and fairly consistent intervals. However, some signals that vary in shape and or interval will yield less useful results. For example, a polymorphic ventricular tachyarrhythmia, or a conducted supraventricular arrhythmia causing wide cycle-to-cycle interval variability, would have an R[n] function that may be low all the way across graph 106. Such an outcome may be used to generate a null rate, indicating no conclusion could be drawn. Alternatively, in another example, a rate may be identified using a highest peak away from that at 110, but with a very low confidence measure. Hence the second rate analysis may not yield a result in some circumstances for some patients, so it may be desirable to retain a primary rate analysis via cycle detection.

Figure 5:
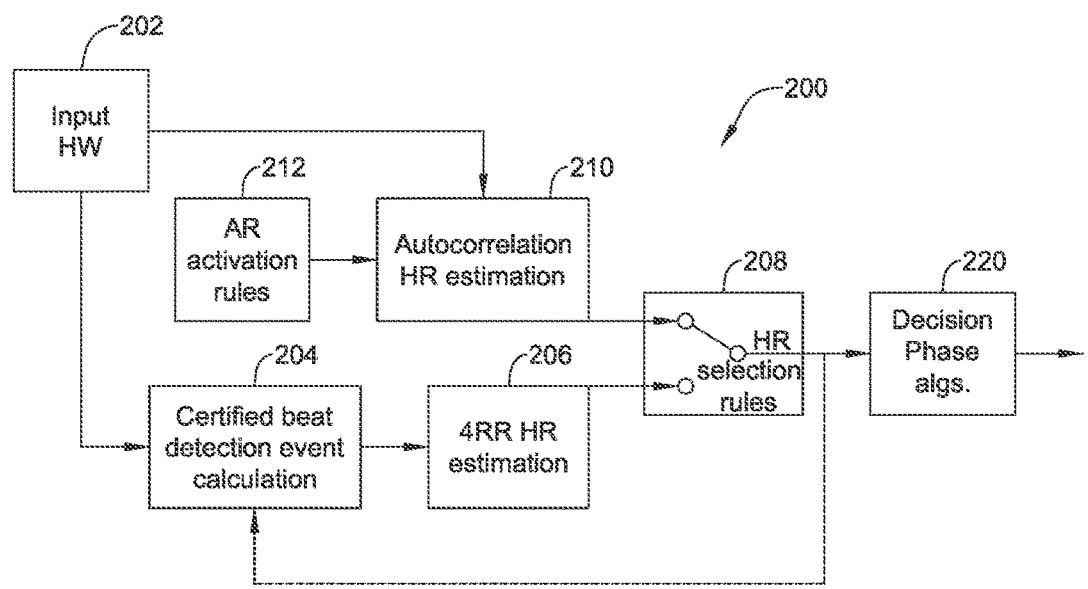
FIGS. 5-8 show illustrative methods in block flow form.
Figure 6:
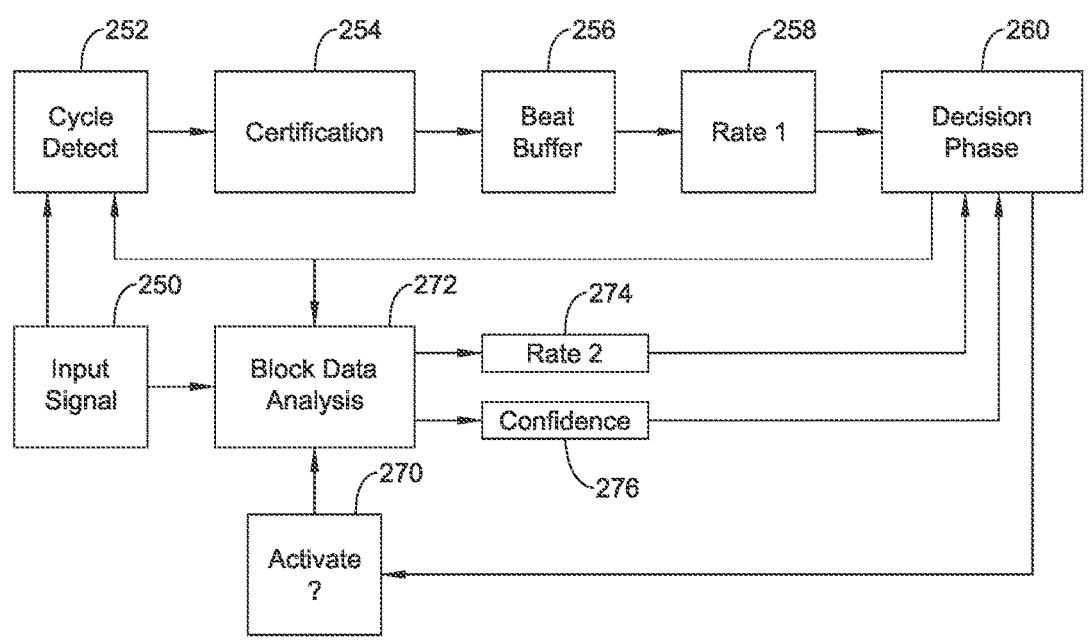
Figure 7:
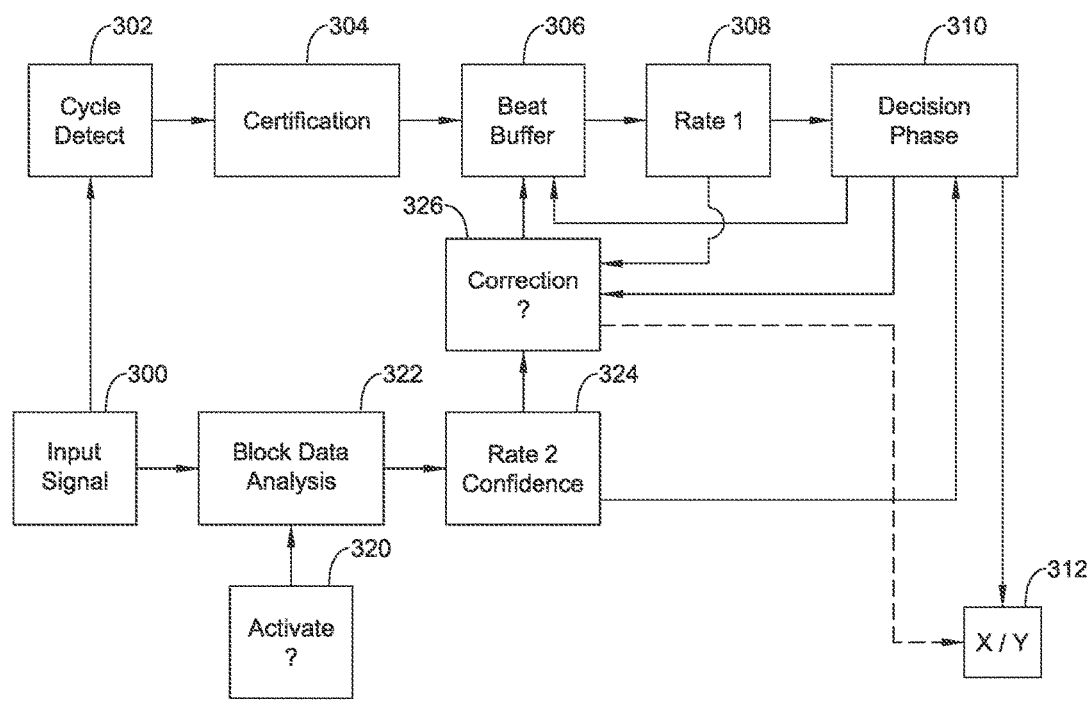

FIGS. 5-7 show illustrative methods in block flow form. In FIG. 5, the method 200 starts with an input signal 202 which may come from the device hardware, such as an input block comprising DC filtering capacitors, one or more amplifiers, and sense signal selection switches (or a multiplexor) for those devices having multiple available sensing vectors, for example. The input signal 202 in this example is a cardiac electrical signal. In other examples, other signals, such as those from sensors for one or more of blood pressure, heart sounds, respiration, motion, pulse oximetry, chemical/chemical changes, etc., may be included.

The signal is passed to a cycle-detection based processing sequence, as noted at 204. The cycle-detection sequence 204 may include, for example, cardiac cycle detection and certification of detected cycles, as indicated at 204. From the certified detected cycles an average interval is calculated at 206, which may be, for example, an average of four intervals between certified cycles, QRS complexes, or R-waves, for which "4RR" is a shorthand. Other waves of the cardiac cycle may be detected, in different quantities, as desired.

A heart rate selection block is shown at 208. Block 208 may select between the rate from block 208 and a rate determined by use of an autocorrelation function 210, and passes the result forward to a decision phase 220, which may be much as described above relative to FIG. 2. The decision phase 220 may further perform data correction described below to change stored rates or detected events or the X/Y filter contents, among other modifications, when using the second heart rate estimate from block 210 instead of or in addition to the first heart rate estimate from block 206.

The autocorrelation function 210 may be performed periodically or in response to detected conditions, based on a set of autocorrelation activation rules noted at 212. The autocorrelation analysis may be as disclosed in one or more of U.S. patent application Ser. Nos. 14/819,817, 14/819,851, and 14/819,889, which provide numerous additional examples and detailed discussions. FIG. 4, above, provides a summary level view of an autocorrelation function.

It should be noted again that the rate estimate from block 210 may use an analysis other than autocorrelation. For example, a device as in FIG. 1 may communicate to a second implantable device, such as a subcutaneous monitor, a transvenous pacemaker, or a leadless cardiac pacemaker implanted inside the heart, to obtain a rate therefrom. See, for example, US PG Patent Application Publication 20150196758, titled SYSTEMS AND METHODS FOR DETECTING CARDIAC ARRHYTHMIAS, the disclosure of which is incorporated herein by reference. Other examples may rely on a different data type, such as blood pressure data, pulse oximetry, cardiac motion, or heart sounds, for example, to determine or estimate cardiac rate, where the sensor for the second rate may be part of the same device as is performing the analysis of FIG. 5, or may be provided by a separate device located elsewhere in the patient's body, with the rate obtained using wireless or tethered communication, or by conducted communication through the body.

Some illustrative rules for activation at block 212 may include the following:

A finding that the rate calculated at block 206 is above a threshold, either in a single measurement or repeatedly.

A finding that an X/Y filter used in a device has reached or crossed a threshold.

A periodic check of rate may be performed by, for example, activating the second rate block 210 as relatively long intervals (two to thirty seconds, for example) and comparing to the rate calculated at block 20. If the rates are different (for example, more than 10 to 30% apart, or off by at least 30-60 bpm), a shorter interval activation (500 ms to 2 seconds, for example) of block 210 may be initiated.

A finding that noise or overdetection or a combination thereof is being observed. For example, if two consecutive detected cardiac cycles are found to be noisy or caused by noise and fail certification, or if three out of seven consecutive detected cardiac cycles are found to be overdetection and fail certification, or other similar boundaries.

A long pause between detected cycles takes place.

A change in signal quality for the signal generated by the input hardware 202, for example as described in copending U.S. Patent Application 62/245,757, titled SIGNAL QUALITY MONITORING FOR MULTIPLE SENSE VECTORS IN CARDIAC DEVICES, the disclosure of which is incorporated herein by reference. This may include a drop in signal amplitude or a change in signal spectral content, and/or other factors noted in the copending application.

A comparison between cardiac-cycle based rate counting and observation of an activity sensor output which shows a disparity. For example, patient activity can be tracked with temperature, motion, or other sensors; when the patient is active according to such sensors, but the observed cycle rate is low, or, alternatively, when the patient is inactive according to such sensors but the observed cycle rate is high, a disparity would be found.

A determination that the patient has changed posture, where, for example, the change in posture may affect sensing signal quality and so a comparison of rate analyses can be useful.

In any of the above circumstances, a new activation can be applied, once, repeatedly for a preset time period, or repeatedly until some event occurs. Active engagement simply means sufficient availability to be used in the later decision phase at 220. For example, a second rate may be sufficiently active if results are provided at intervals of 500 milliseconds up to four seconds, or longer as desired; in some example, the second rate may be provided about once every 1-2 seconds. In some examples, such as after a change in posture, a single confirmation that the first rate calculation, based on detecting cardiac cycles, for example, continues to be valid, may be performed and so a single activation is made.

As noted, in some examples, activation may occur until an event takes place, such as expiration of a timer or one of the following:

If the two heart rates provided at blocks 206 and 210 are similar

If a condition, such as elevated rate or an X/Y filter in excess of a threshold, or an observed disparity between measures of activity and rate, no longer exists (for at least a minimum period of time in some examples)

Assuming noise or overdetection was a trigger for activation at 212, if beat certification resumes consistent certification indicating an end to noise or overdetection Assuming a drop in amplitude or signal quality was a trigger for activation at 212, if the amplitude increases or signal quality improves The end of active engagement may entail complete disabling of the second rate calculation 210, or may indicate a longer period between iterations of the second rate calculation. For example, when "active", a second rate calculation may occur or be obtained at 500 ms to two second intervals; when inactive, the second rate calculation may occur or be obtained at longer intervals such as four to thirty seconds.

FIG. 6 shows another example. Beginning with the input signal 250, a cycle detection method is applied at 252, leading to certification phase 254. The outcomes from certification phase are used to populate a beat buffer 256, from which a first rate, "Rate 1" is calculated as indicated at 258. Rate 1 is then provided to the decision phase at 260.

In another data stream, the input signal 250 passes to a block data analysis 272, which performs analysis according to an activation schedule 270 and yields an output, Rate 2, at 274. Rate 2 may be associated with a confidence measure 276 as described above in reference to FIG. 4. The decision phase 260 may use the confidence 276 to determine which of Rate 1 or Rate 2 to rely upon.

The decision phase 260 may use analysis of Rate 1, or of the beat buffer 256, alongside Rate 2 274 and or confidence 276, for example, to determine whether to trigger more frequent activation 270 of the block data analysis 272. For example:

If either Rate 1 or Rate 2 exceeds a predetermined threshold, and the confidence 276 is above a threshold, more frequent activation 270 may be called upon for a period of time until either the predetermined threshold is no longer exceeded, or the confidence 276 drops;

If the decision phase determines that an X/Y filter has begun filling, or has reached a first threshold, more frequent activation 270 may be called upon until the filter X/Y drops below a second threshold, unless the confidence 276 is low; and/or If the beat buffer, which in one example may include both certified and not-certified cycle markers (including, for example, noise or overdetection markers), contains more markers for a period of time than would be predicted given Rate 2, more frequent activation may be called.

Other examples noted above for de-activating, or reducing the frequency of activation, of a second cardiac rate measurement, may be used as well.

FIG. 7 shows another example. Here again, the input signal 300 goes through cycle detection 302 and certification 304 to populate a buffer 306. The buffer 306 can be used to calculate a first rate, Rate 1, 308 for use by the decision phase 310. The decision phase 310 may mark events in the buffer as treatable or non-treatable in this example; in the prior example of FIG. 6, the buffer may simply be a beat buffer indicating time stamps and, as desired, associated shape data for certified detected cycles. The decision phase 310 may keep a separate X/Y filter (or plural X/Y filters) for marking treatable or non-treatable indications.

Further in this example, an activation block 320 may trigger second rate calculation via block data analysis at 322 (though other second rate calculations noted above may instead be performed). The analysis at 322 yields a second rate, Rate 2, which may be associated with a confidence measure as noted at 324.

The decision phase 310, or a separate logic block 326, can decide whether correction is needed in response to a discrepancy between Rate 1 and Rate 2. Correction may take place using the beat buffer 306, or may occur on the separately provided X/Y filter, or both, as desired. Some examples of correction in the beat buffer are shown below. Additional examples directed at the X/Y filter are shown in U.S. Patent Application 62/262,037, titled METHODS AND DEVICES COMBINING MULTIPLE CARDIAC RATE MEASUREMENTS WITH ACTIVATION AND ARRHYTHMIA ANALYSIS CORRECTION, the disclosure of which is incorporated herein by reference.

Figure 8:
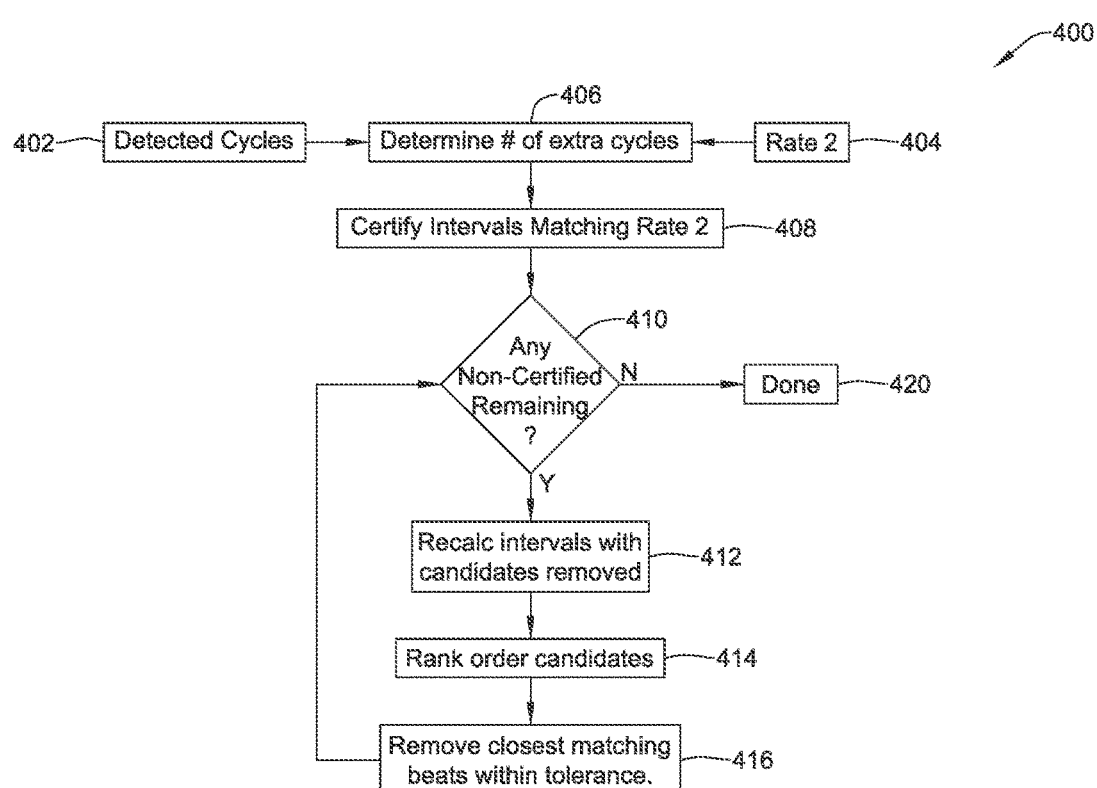

FIG. 8 shows an illustrative method is block flow form. In the method 400, a set of detected cycles 402 and a rate, Rate 2 404 serve as inputs to block 406. Rate 2 404 may be, for example, a cardiac rate measurement generated by a non-cycle-detection method (such as the method illustrated and discussed with reference to FIG. 4, above). At block 406, the method determines how many extra cycles are in the set of detected cycles 402, using Rate 2 404. For example, in block 406, the time period spanned by the set of detected cycles 402 is determined, and a quantity of expected cardiac beats is calculated by multiply the time period by Rate 2 404. For example, if ten detected cycles are brought into the method at block 402, spanning a period of four seconds, and Rate 2 is 90 bpm, the expected quantity of detected cycles would be 90 bpm times four seconds, yielding six expected cycles. Given ten detected cycles in the time period, there would be four extra cycles found at block 406.

Next, the intervals between the detected cycles 402 are checked to see if any match an expected interval generated using Rate 2 404. The step at 408 may apply a plus/minus range when comparing to the expected interval, for example, plus/minus two to fifteen percent, or plus/minus 10 to 100 milliseconds may be used, or wider or narrower bounds as desired. If, for example, Rate 2 404 is 90 bpm, then the expected cycle length to match that rate would be about 667 milliseconds; using a plus/minus range of 40 milliseconds, any interval in the range of 627 to 707 milliseconds would be certified at block 408 in this example.

Next, at block 410, an iterative proves begins by determining if there are any non-certified intervals remaining. If there are non-certified intervals remaining, then candidate detected cycles are identified and intervals are recalculated, as noted at 412. Next, the candidate cycle detections are rank ordered based on how the remaining intervals are affected, as indicated at 414. Those removals that result in matching intervals (again within the tolerance boundaries) are removed at 416, and the now matching intervals are certified. The method returns to block 410 to determine whether there continue to be any non-certified intervals. The process may be performed in ordered fashion by starting with a first in time interval and determining what combination of subsequent intervals may be combined in order to yield a desired average interval.

Figure 9:
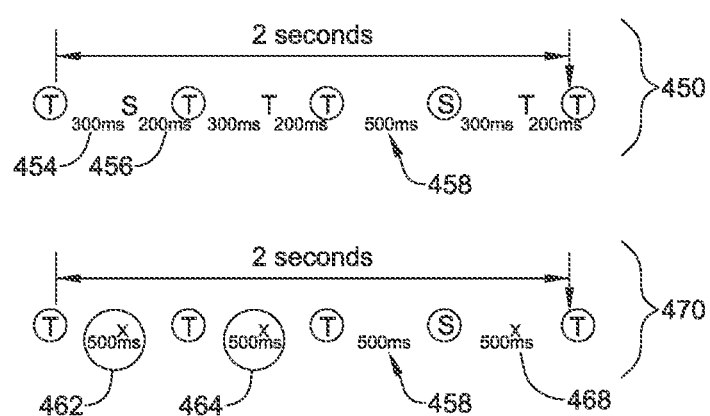
FIG. 9 shows a beat counter correction method as operated.

FIG. 9 is illustrative. Here, an original detected cycle set is shown at 450, with detected cycles and intervals marked. A two second window of the beat buffer 452 is analyzed. The set of cycles in time interval 452 may be the "detected cycles" provided as inputs at block 402 of the method in FIG. 8, for example. In this example, the value for Rate 2 referred to in FIG. 8 would be 120 bpm, meaning that the expected interval is 500 milliseconds. Therefore the first step in the method is to certify the interval shown at 458, which matches the expected intervals.

Next, beginning on the left side of the page, the first interval in time is noted at 454. When added to the next-in-time interval 456, the result is the expected value of 500 milliseconds. Therefore the intervening cycle detection separating intervals 454 and 456 is marked as an overdetection, and a combined interval is generated as noted at 462 having the expected interval value of 500 milliseconds. Interval 462 would then be certified. The process would repeat itself to generate interval 464. Interval 458, having already been certified, would be left undisturbed, and another combined, certified interval is noted at 468. A new set of cycle detections and intervals is generated in this manner to generate a corrected beat buffer 470.

If desired, the method may also re-mark or recalculate the contents of an X/Y Filter after correction of the beat buffer, for example as shown in U.S. Provisional Patent Application 62/262,037, titled METHODS AND DEVICES COMBINING MULTIPLE CARDIAC RATE MEASUREMENTS WITH ACTIVATION AND ARRHYTHMIA ANALYSIS CORRECTION, the disclosure of which is incorporated herein by reference.

The illustration in FIG. 9 works out rather neatly for illustrative purposes. In application, however, it is likely that in some instances the detected cardiac cycles will provide intervals that simply do not match, whether alone or in combinations, an expected interval for "Rate 2". To address overall mismatch, the method may adopt one of several solutions. In some examples, a set of detected cardiac cycles is analyzed first to determine how many "extra" detections have occurred in the time period the set of cycles spans, and a best fit is achieved by removing the number of extra detections in a manner that minimizes the divergence of the remaining intervals from the expected average interval— that is, combinations of cycle detection removals are considered until a least-wrong fit is obtained. In another example, a system that uses an N-interval average to calculate rate may observe which combination of cycle detections can be removed to achieve a best fit, over time, to the expected N-interval average. For example, if a 4-interval average is used to calculate rate, then the cycle detection removals performed in accordance with FIGS. 8-9 would be done in order to achieve a 4-interval average that matches the expected average interval calculated using Rate 2.

Figure 10:
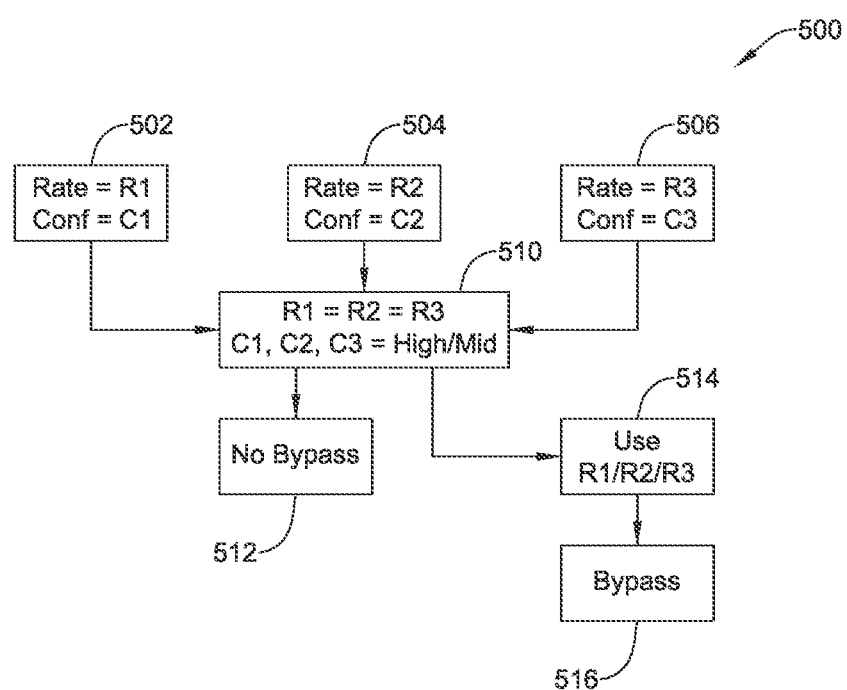
FIG. 10 shows an illustrative method in block flow form.

FIG. 10 shows an illustrative method in block flow form. This method is operable to bypass certain elements the decision phase processes (such as block 310 in FIG. 7, above) when a second cardiac rate calculation results in persistent outcomes that are repeated and similar, within preset bounds. As discussed above with reference to FIG. 4, a non-cycle-detection based rate estimate may be calculated at intervals, for example every one to three seconds (or more or less), and may include both a rate output and a confidence measure. The rate measurement may be an asynchronous rate measurement in that it is not synchronized to cardiac cycle detection. The method of FIG. 10 takes advantage of the repeated delivery of rates and/or confidence to bypass other parts of the decision process of an illustrative example.

In the method 500, at least two, or in the example, three, outputs of an asynchronous rate measurement, as indicated at 502, 504, 506. Next, it is determined whether the three rates, R1, R2, R3 are all the same, within predefined boundaries, as indicated at 510. In an example, the rate comparison at 510 may use a tolerance rating of, for example, plus/minus ten percent, or plus minus a fixed quantity, using measurements in terms of R-R intervals or BPM. For example, to satisfy R1=R2=R3, in one embodiment, the largest of the absolute values of the values {(R1−R2), (R1−R3), (R2−R3)} would be less than 30 milliseconds. Other examples may use different thresholds to determine if the two or more rates are sufficiently similar.

Optionally, and as indicated at 510, the method may also refer to the confidence measures for each of the outputs of the asynchronous rate measurement 502, 504, 506, and call for medium to high confidence for each. If the conditions are 510 are not met, then device operation goes on without any bypass as indicated at 512. If conditions at 510 are met, then the average, or simply one of, R1, R2 and R3 is then used as indicated at 514 to bypass 516 other decision processes.

In an illustrative example, if the used rate R1/R2/R3 is above a first threshold for ventricular fibrillation, the method bypasses 516 other analyses and determines that high voltage therapy is to be prepared and delivered. Continuing the first non-limiting example, if the used rate is in a range for ventricular tachycardia treatable by anti-tachycardia pacing (ATP), the method bypasses 516 other analyses and determines that ATP is to be delivered. Finally in the first non-limiting example, if the used rate R1/R2/R3 is below a tachyarrhythmia threshold, the method bypasses 516 other analysis and ensures that no therapy is delivered.

Bypass 516 may take several forms including:

Activation or deactivation of a tachyarrhythmia mode in which enhanced analysis and data recording or episode declaration is performed, and/or during which preparations for therapy (such as charging a therapy delivery capacitor) may take place.

Automated assertion of charge begin for devices that deliver high voltage therapy after charging a capacitor, if the rates R1/R2/R3 are above a threshold.

Automatically aborting a charging operation or tachyarrhythmia mode if the rates R1/R2/R3 are below a threshold.

Automatically calling for therapy, for example if ATP is available in a system and can be delivered on-demand, ATP may be initiated Inhibiting a therapy such as ATP or defibrillation Similar operations may be implemented for a monitoring system that would record or communicate data, or generate an alert or alarm. In addition, for a device having drug delivery available, inhibition or activation of drug delivery may likewise be performed in similar fashion to the inhibition or activation of ATP or defibrillation therapy.

Rather than requiring unanimity of the observed rates, an M of N logic may be used, for example, calling for 2 of 3, or 5 of 6, or some other fraction and group size, to agree closely and with relatively high confidence. The bypass may remain in place until rate matching is no longer occurring, or until confidence drops, or, until the calculated rate rises above a threshold or drops below a threshold. Moreover, bypass may terminate if the rates gradually increase beyond a threshold percentage or amount. For example, if a bypass is activated when the calculated rate is 80 bpm, and the calculated rate using the second analysis rises by more than 25% (here, above 100 bpm), the bypass may terminate until it can be newly applied.

Figure 11:
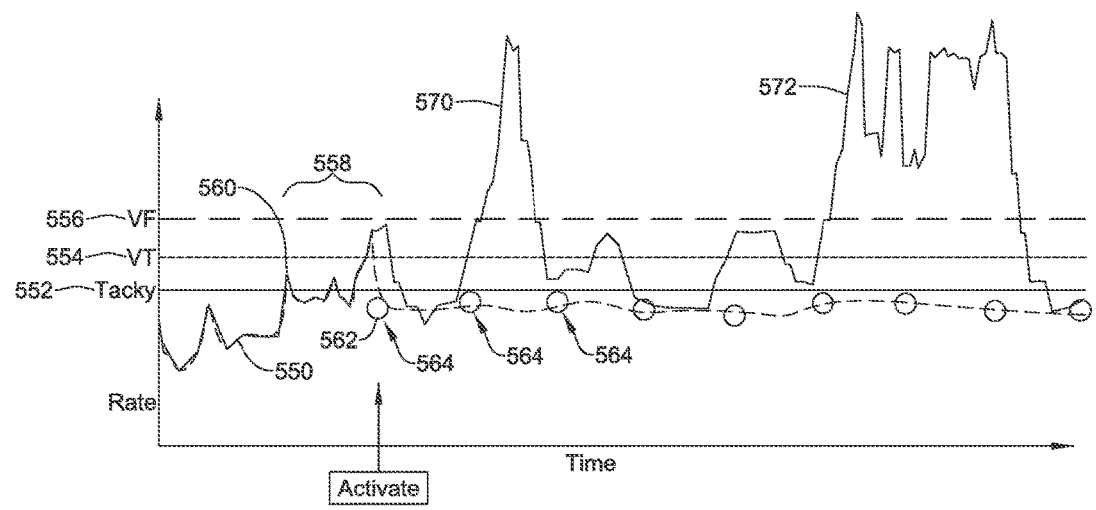
FIG. 11 shows in graphic form operation of a bypass method.

FIG. 11 shows in graphic form operation of a bypass method. In this example, the graph at shows rate on the vertical axis and time on the horizontal axis. A cardiac rate as calculated using a cycle detection process is shown at 550, for comparison against a tachycardia or high rate threshold 552. Threshold 552 may be used to place the device in an alert state, or may be used to make changes in the manner of analysis, such as triggering a second rate analysis or modifying the manner of cycle detection. Use of a rate boundary to trigger a second rate analysis is discussed in some examples in U.S. Provisional Patent Application 62/262,037, titled METHODS AND DEVICES COMBINING MULTIPLE CARDIAC RATE MEASUREMENTS WITH ACTIVATION AND ARRHYTHMIA ANALYSIS CORRECTION, the disclosure of which is incorporated herein by reference. Changes to a manner of cycle detection in response to rate are discussed, for example, in U.S. Pat. No. 8,565,878, titled ACCURATE CARDIAC EVENT DETECTION IN AN IMPLANTABLE CARDIAC STIMULUS DEVICE, the disclosure of which is incorporated herein by reference.

A VT threshold is shown at 554, and a VF threshold is shown at 556. When the cardiac rate is between the VT threshold 554 and VF threshold 556, enhanced analysis may be performed to distinguish supraventricular fast rhythms, such as exercise induced tachycardia or certain conducted atrial arrhythmias, from treatable ventricular fibrillation or polymorphic ventricular tachyarrhythmia, for example, using various methods such as those shown in U.S. Pat. No. 7,330,757, titled METHOD FOR DISCRIMINATING BETWEEN VENTRICULAR AND SUPRAVENTRICULAR ARRHYTHMIAS. For example, cardiac signal morphology matching to a template, or to adjacent-in-time cardiac cycles, or cardiac signal width (such as QRS or R-wave width) may be analyzed. When the cardiac rate is found to be above the VF threshold 556, the patient's cardiac condition may be considered treatable regardless of secondary factors such as morphology, width, etc.

Beginning at about time 558, malsensing begins to occur with the cardiac cycle detection, and so rate 550 climbs up, extending above the VT threshold 554 and above the VF threshold 556. These excursions may lead to incorrect therapy decisions.

However, the crossing of the Tachy threshold 552, indicated at 560, triggers a second analysis with the circles shown at 562 representing rate as calculated using a second rate estimate. The second analysis may include obtaining a rate from a second device, or, in several examples, using a method which is not reliant on cardiac cycle detections. One such method is shown in FIG. 4, above, and various methods are noted above.

At 564, three consecutive rate measurements from the second analysis are reviewed using the method of FIG. 10. The three rates 564 are very similar. Optionally, it may be assumed for the example, one or all of rates 564 are generated with medium or high confidence (again using the example of FIG. 4 and associated discussion, above). As a result, decisions based on the cycle-based rate 550 are bypassed. As time moves forward, the bypass continues including during a short excursion above the VF threshold 556 shown at 570, and during a longer excursion shown at 572. As a result, inappropriate therapy is avoided.

In other examples, the second analysis rates 564 may be used to correct beat buffers as illustrated in FIGS. 8-9 above. In still further examples, the X/Y filter or other counter that tracks decisions may be adjusted as time goes on, to correct rather than bypass the decision phase, as discussed in U.S. Patent Application 62/262,037, titled METHODS AND DEVICES COMBINING MULTIPLE CARDIAC RATE MEASUREMENTS WITH ACTIVATION AND ARRHYTHMIA ANALYSIS CORRECTION, the disclosure of which is incorporated herein by reference.

Figure 12:
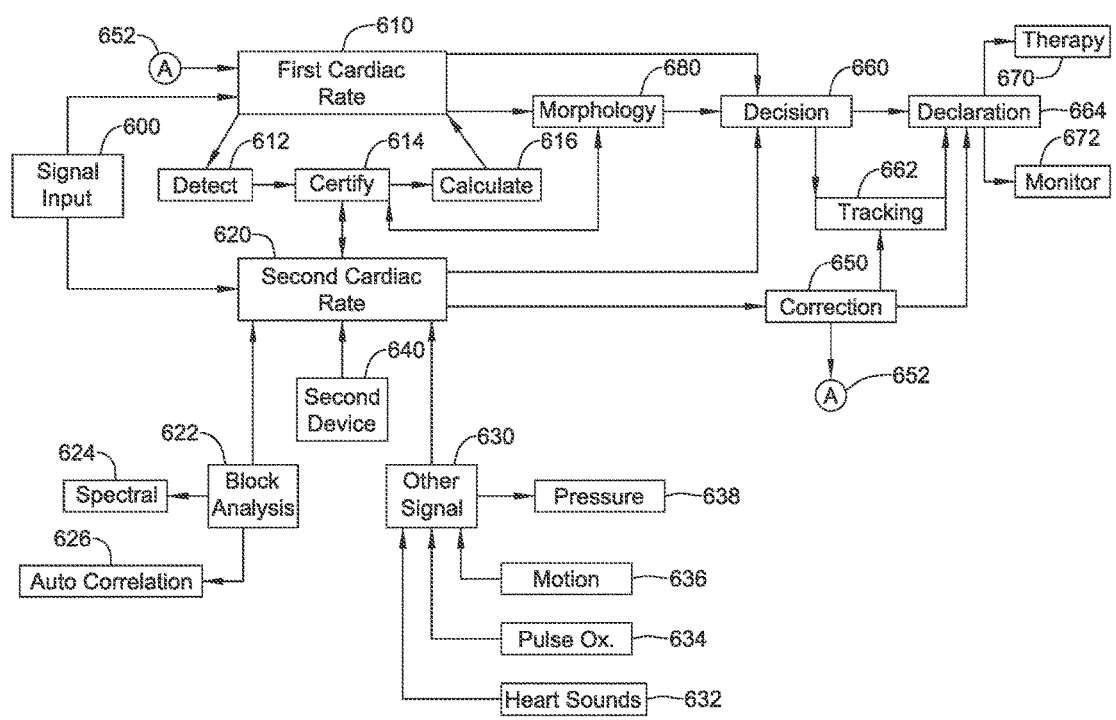
FIGS. 12-14 show illustrative examples.
Figure 13:
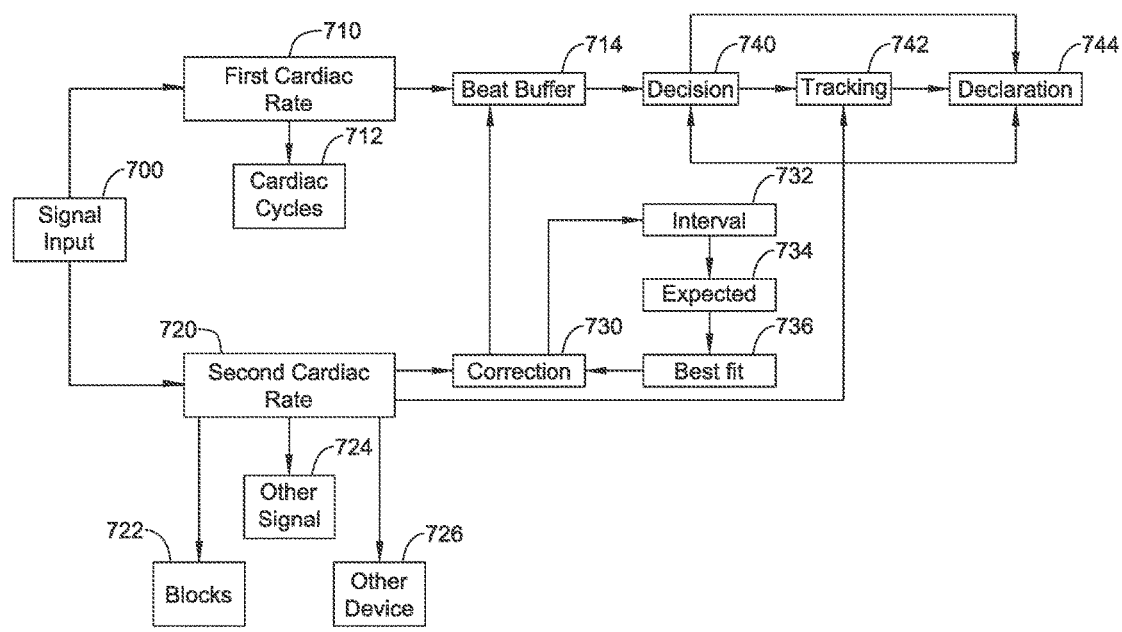
Figure 14:
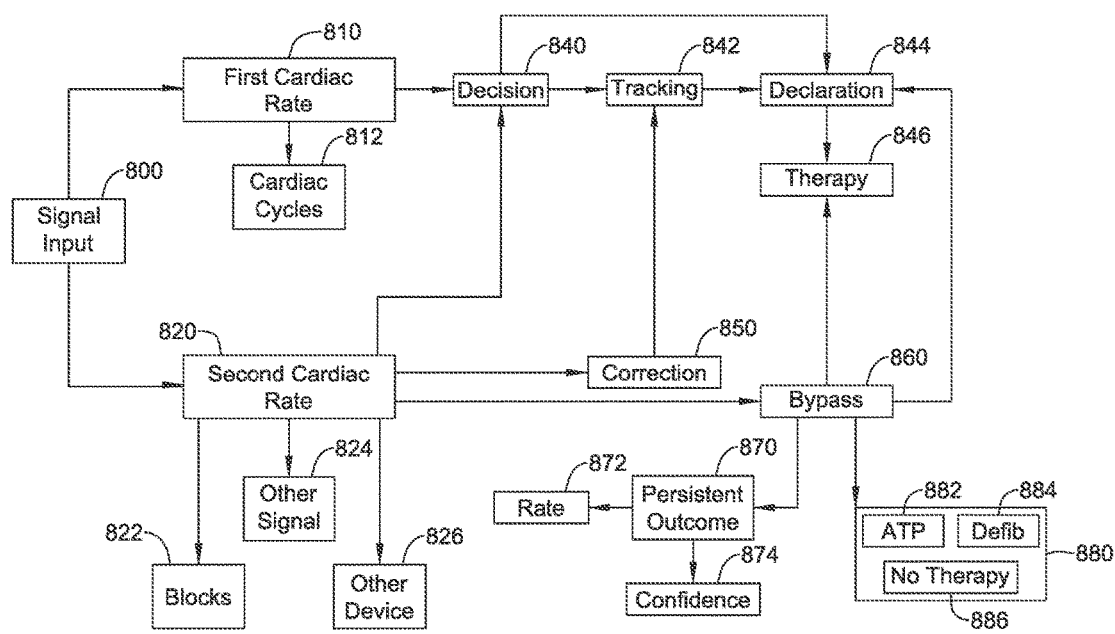

FIGS. 12-14 show illustrative examples in block form. Each block may represent a step in a method or may represent a dedicated circuit, set of instructions for operation by a processor or controller, or a combination of circuitry and instructions.

Referring first to FIG. 12, a signal input is illustrated at 600. The signal input block 600 may comprise, for example, switches for selecting a signal vector (if multiple sense vectors are available such as shown above in FIG. 1), filtering, amplification, and, optionally depending on system configuration, analog to digital conversion circuitry.

The signal input block 600 provides signal to a block for the first calculation of cardiac rate at 610. Block 610 may represent, for example, dedicated circuitry and/or executable instructions or instruction sets stored in memory for performing the detection of cardiac cycles at 612. Detected cycles from block 612 may undergo certification at 614. The certified cycles from block 614 may be used to calculate intervals which can be averaged at 616 to provide a first rate estimate that can then be provided by block 610 to a decision stage 660, explained below.

The signal input block 600 may also provide signal to a block for the second calculation of rate at 620. Block 620 may represent, for example, dedicated circuitry and/or executable instructions or instruction sets stored in memory for execution to provide several variants on the second calculation. Block 620 may operate using block data or signal analysis 622 using, for example, a spectral analysis 624, in which an average or peak spectral content may be determined for a block of data to yield a frequency of cardiac events. Block data or signal analysis 622 may instead use an autocorrelation function 626 such as that explained above with reference to FIG. 4 and/or in copending U.S. patent application Ser. Nos. 14/819,817, 14/819,851, and 14/819,889, the disclosures of which are incorporated herein by reference.

Block 620 may, instead, rely on a non-cardiac-electrical signal, as indicated at 630—that is, the cardiac electrical signal may not be the focus of block 620. Some examples in block 630 may include the use of heart sounds 632, pulse oximetry 634, cardiac motion 636, and/or blood pressure data 638. In still a further alternative, block 620 may obtain a cardiac rate estimate using a second device 640 such as by, for example, communicating with a second device that can provide a cardiac rate estimate. Some examples include, for example, a separate rate monitor such as a wearable or implantable cardiac monitor, pulse oximeter, and/or blood pressure monitor, for example. In one example, a device having the functional and circuitry blocks illustrated in FIG. 12 may be an implantable subcutaneous-only defibrillator (such as shown in FIG. 1, above), and may communicate using wireless or conducted communication with a separate transvenous or intracardiac device such as a leadless cardiac pacemaker implanted in the heart.

In one example, the second cardiac rate 620 is referenced and used by the certification stage 614. For example, the certification stage may observe whether a set of detected cycles from block 612, and/or a set of intervals between such cycles, correspond with the calculated second cardiac rate from block 620. If not, then one or more of the detected events from block 612 may be flagged as an overdetection or noise beat and not certified. In making determinations as to which detected cardiac cycle(s) to flag as overdetections or noise, the certification block 614 may reference or obtain data from a morphology analysis block 680. The morphology analysis block 680 may compare data for detected cardiac cycles to one or more stored templates and/or may compare data from one cardiac cycle to another cardiac cycle using, for example, one or more of difference of area analysis, correlation waveform analysis, wavelet analysis, principal component analysis, signal width measurements, etc. Better matching cardiac cycle detections, whether matching one another or a stored template, or those having narrower widths suggestive of true QRS complex or R-wave detections may be retained while cardiac cycle detections with lower matching scores or shapes not suggestive of true QRS complexes or R-waves may be preferentially discarded. FIGS. 8-9 show examples where one or more detected cardiac cycles are not certified for use in rate calculation 616.

Blocks 610 and 620, as well as the morphology block 680, may provide information to the decision block 660, where determinations are made as to whether or not a potentially treatable (for a therapy system, for example), or recordable (for a monitoring system, for example) cardiac rhythm or arrhythmia is occurring. The decision block 660 may rely on calculated or obtained cardiac rate measurements as well as cardiac signal morphology metrics such as template matching (to stored or dynamic templates and/or between near in time cardiac cycles), signal width, amplitude, or other measures from the morphology block 680. The decision block 660 may use a tracking block 662, which may comprise an X/Y filter, for example. In the example shown, if the rates output in blocks 610 and 620 diverge, a correction block 650 may be used to change the decision block 660 and/or tracking block 662 (including the X/Y filter). Various examples of the operation of a correction block 650 operating to affect tracking 662 are also shown in U.S. Patent Application 62/262,037, titled METHODS AND DEVICES COMBINING MULTIPLE CARDIAC RATE MEASUREMENTS WITH ACTIVATION AND ARRHYTHMIA ANALYSIS CORRECTION, the disclosure of which is incorporated herein by reference.

The decision block 660 and tracking block 662 provide information for a declaration block 664 which declares whether one of therapy activities 670 or monitoring activities 672 should be engaged. For example, therapy and/or therapy preparation may be commanded by block 664 via block 670 when the data provided to block 664 satisfy therapy requirements. Data storage, alert annunciation, or message communication via block 672 may be initiated when monitoring thresholds are met. For example, the X/Y filter used by the tracking block 662 may be required to reach a threshold (8/12, 12/16, 18/24, 30/40, for example), and the decision block 660 may be required to show that the most recently analyzed data supports a conclusion that an arrhythmia is occurring, and such conditions may be required to meet a persistence criteria, to satisfy therapy requirements applied by the declaration block 664. Other therapy requirements may be used.

The data correction block 650 may also be used to affect the first cardiac rate block 610 by, for example, calling for re-analysis of detected and/or certified cardiac cycles, or to supplant a calculated rate from block 616.

FIG. 13 shows another illustrative example. Similar to FIG. 12, a signal input 700 provides data for a first cardiac rate calculation 710 that may rely on cardiac cycles 712 that undergo detection, certification and rate computation. In this example, the first cardiac rate block 710 generates a beat buffer at 714.

The second cardiac rate block is also noted at 720 and block data 722, data from other signals 724, or data from other devices 726 to calculate or obtain rate information. The second cardiac rate block is used to provide information for a correction block 730 that analyzes the beat buffer 714 in light of the rate provided to it by the second cardiac rate block 720.

The correction block 730 may operate by observing a set of intervals 732 defined by detected cardiac cycles in the beat buffer 714. These are then compared to an expected set of intervals generated using the second cardiac rate from block 720, as indicated at 734. A best fit can then be generated as noted at 736. FIGS. 8-9 provide an example of such an operation.

The beat buffer provides information for the decision block 740, which may rely on a tracking block 742. Blocks 740 and 742 provide inputs to a declaration block 744 that may drive therapy and/or monitoring activities (not shown in FIG. 13 but similar to that of FIG. 12). The second cardiac rate 720 may again be used to affect operations in one or more of the decision block 740, tracking 742, and declaration block 744, in addition to being used by the correction block 730 to make changes as needed in the beat buffer 714.

FIG. 14 shows another illustrative example. This example again starts with a similar set of blocks as FIGS. 12-13. The signal input 800 may provide information/data to the first cardiac rate block 810 that operates using cardiac cycle detection 812. The signal input block may also provide data to a second cardiac rate block 820, which again may use blocks of data 822, signals other than the cardiac electrical signal 824, or signals from another device 826. The two rate blocks 810, 820 provide information to a decision block 840, that operates along with a tracking block 842 to provide information to a declaration block 844 which in turn controls a therapy block 846 (a monitoring block may replace the therapy block 846 in other examples). A correction block 850 may use an output from the second cardiac rate block 820 to correct the tracking data at 842 (or X/Y filter, not shown in FIG. 14) and/or may also affect the decision block 840 and first cardiac rate block 810 or beat buffer (not shown).

The second cardiac rate block 820 may also provide an output to a bypass function 860. The bypass function 860 may force behavior in the declaration block 844, requiring automatic declaration of a treatable condition or preventing such declarations. The bypass function 860 may also or instead go directly to the therapy block 846 to trigger therapy or therapy preparations, to stop therapy preparations, or to interrupt or inhibit therapy delivery.

In one example, the bypass block 860 may call for persistent outcomes 870 from the second rate block 820, such as calling for plural analysis (two or more iterations, such as shown in FIGS. 10-11, above) to yield similar rates 872, optionally with high confidence 874. In another example, the bypass block 860 may perform its own declaration analysis as indicated at 880 by classifying the rate 872 into a category. For example, in a device having each of ATP and defibrillation therapy available, the bypass block may classify the detected cardiac signal depending at least in part on rate 872 into one of an ATP rate zone 882, a defibrillation zone 884, or a no therapy zone 886. The bypass function 886 would then command the declaration block 844 and/or therapy block 846 to do one of deliver ATP, prepare for and/or deliver defibrillation, cease preparations for therapy, and/or inhibit therapy delivery, according to which zone 882, 884, 886 applies.

Additional examples for combining together first and second cardiac rates are shown in U.S. Patent Application 62/262,037, titled METHODS AND DEVICES COMBINING MULTIPLE CARDIAC RATE MEASUREMENTS WITH ACTIVATION AND ARRHYTHMIA ANALYSIS CORRECTION, the disclosure of which is incorporated herein by reference. These examples may be used in various combinations. For example:

An X/Y filter correction method shown in the 62/262,037 application may be used in combination with a bypass block as illustrated in FIG. 14. For example, the X/Y filter may be corrected in response to a single iteration of a second rate calculation and the X/Y filter may be bypassed after 2 or more persistent rate results from the second rate calculation.

An X/Y filter correction method shown in the 62/262,037 application may be used in combination with beat buffer correction as illustrated above. In this way, both current and previously generated data may be readily corrected throughout the arrhythmia analysis architecture.

In another example, the beat buffer correction methods shown above may be used to correct data that is still in-process in the arrhythmia analysis architecture in response to a second rate calculation being different from a first rate calculation and, results from the beat buffer analysis may be bypassed after 2 or more persistent rate results from the second rate calculation.

Further combinations may also be used.

Some implementations include operational circuitry for receiving a signal from implantable electrodes, processing the signal and analyzing the processed signal to make decisions such as whether to store data or deliver therapy. Operational circuitry may be housed in a canister or canisters. The operational circuitry may include a controller (such as a microcontroller or microprocessor, or simply an application specific integrated chip (ASIC) such as an analog, mixed signal, or digital ASIC). The operational circuitry may include suitable analog and/or digital circuits needed for signal processing, memory storage and generation of high-power electrical, low-power electrical and/or non-electrical outputs. The operational circuitry may include suitable battery technology for an implantable device (rechargeable or primary cell), with any of numerous examples well known in the art, and may use various capacitor technologies to assist in the short term build-up and/or storage of energy for defibrillation or other output purposes.

Implantable or wearable components may be manufactured with biocompatible materials suitable for implantation or tissue contact, such as those widely known, along with coatings for such materials, throughout the art. For example, implantable devices can be made using titanium, with a titanium nitride or iridium oxide (or other material) coating if desired, and implantable leads can be formed with a biocompatible material such as a polyether, polyester, polyamide, polyurethane, polycarbonate, silicon rubber and blends or copolymers thereof. Alternatively, other biocompatible materials such as silver, gold, titanium, or stainless steel such as MP35N stainless steel alloy, or other materials may be used.

In some examples, the system may include one or more sensors to detect signals in addition to the cardiac electrical signal that can be captured using selected combinations of implantable or wearable electrodes. Such additional sensors may include, for example, temperature sensors, accelerometers, microphones, optical sensors and chemical sensors, among others. The programmer 22 and implantable device 12 (FIG. 2) may communicate with one another using, for example and without limitation, inductive or RF telemetry, or any other suitable communication solution, including conducted communication in which a field generated between two electrodes on a first device, either on the skin of the patient or implanted in the patient, is detected by a second device such that the two devices use the patient tissue as a conductive medium for communication. The present invention may be embodied in a system having any such characteristics.

In the following non-limiting examples, various means for performing certain functions are described with reference to block diagrams above. It should be understood, as noted above, that such blocks may represent dedicated circuitry/hardware, stored instruction sets for execution by a processor or controller, and/or combinations thereof.

A first non-limiting example takes the form of an cardiac rhythm management device comprising signal means for receiving an cardiac electrical signal for analysis; a first means for calculating cardiac rate, which generates a first cardiac rate by identifying cardiac cycles; a second means for calculating cardiac rate, without identifying cardiac cycles, which generates a second cardiac rate; and correction means to determine, using the second cardiac rate, whether a set of detected cardiac cycles used by the first means for calculating cardiac rate comprises one or more overdetected cardiac cycles. For example, FIG. 7 shows a system that includes an input signal means 300 (which may include selection, filtering, amplification and/or analog-to-digital conversion circuitry) provides an output for a first means for calculating cardiac rate using cardiac cycle detection (blocks 302, 304, 306 leading to Rate 1 at 308), and to second means for calculating cardiac rate using a different, non-cycle driven analysis such as block data analysis at 322 which provides a second cardiac rate at 324 used by a correction means at 326 to correct the contents of the beat buffer at 306. Details of operation of a correction means are shown in FIGS. 8-9. FIG. 12 also shows an example with an input signal means 600 coupled to a first means for calculating cardiac rate at 610 and a second means for calculating cardiac rate at 620, with correction means at 650 coupled, via A, to the first cardiac rate calculation 610, for correcting data generated therein. FIG. 13 shows another example with the signal input 700 providing data for first cardiac rate means 710 and second cardiac rate means 720, with the second cardiac rate means 720 providing information for a correction means 730.

A second non-limiting example is a cardiac rhythm management device as in the first example, wherein the first means for calculating cardiac rate comprises: detection means to identify cardiac cycles as detected events from within the cardiac electrical signal; certification means for certifying the detected events by identifying and omitting noise and correcting overdetection; and calculation means for calculating a first cardiac rate using an average of intervals between certified detected events; wherein the certification means is configured to correct overdetection identified by the correction means. FIG. 12 shows an example where the first cardiac rate means 610 includes detection means 612, certification means 614, and calculation means 616, with the certification means 614 taking an input from the second cardiac rate means 620.

A third non-limiting example is a cardiac rhythm management device as in the second non-limiting example, wherein: the second means for calculating cardiac rate operates iteratively at an interval using the cardiac electrical signal; and the certification means is responsive to correct previously certified detected events upon iterative operation of the second means for calculating cardiac rate if the correction means identifies one or more overdetected cardiac cycles. FIG. 12, and related description, indicates that the second cardiac rate means 620 may use a block data analysis 622 that can be called at intervals, data from a second device 640 that may be referenced at intervals, or data from a different, non-cardiac-electrical signal 630 which, again, may be referenced at intervals. A detailed example shown in FIG. 8 shows how prior stored data may be assessed to certify selected portions of the cycle-detected signal.

A fourth non-limiting example takes the form of a cardiac rhythm management device as in any of the first to third non-limiting examples, further comprising a morphology analyzer to determine whether detected cardiac cycles match one or more templates; wherein the correction means is configured to rely on outcomes from the morphology analyzer to select which detected events, if any, are overdetections. FIG. 12 shows a morphology analyzer at 680, coupled to a certification block 614 and useful, as described above and recited in this non-limiting example, to assist in the certification step to determine which of a set of candidate detected cardiac cycles should be marked as overdetected. For example, if there are 10 detected cardiac cycles in a period of time for which the second cardiac rate calculated by means 620 indicates only 6 cycles should have occurred, the four detected cycles characterized by the worst or lowest correlation to a stored template, or to adjacent cycles, may be marked as overdetected.

A fifth non-limiting example takes the form of a cardiac rhythm management device comprising: signal means for receiving an cardiac electrical signal for analysis; a first means for calculating cardiac rate by identifying individual cardiac cycles within the cardiac electrical signal, which generates a first cardiac rate; a beat buffer for tracking the identified cardiac cycles from the first means for calculating rate; a second means for calculating cardiac rate, without identifying cardiac cycles using the cardiac electrical signal, which generates a second cardiac rate; a correction means for correcting contents of the beat buffer in response to the second cardiac rate being different from the first cardiac rate. For example, FIG. 7 shows a system that includes an input signal means 300 (which may include selection, filtering, amplification and/or analog-to-digital conversion circuitry) provides an output for a first means for calculating cardiac rate using cardiac cycle detection (blocks 302, 304, 306 leading to Rate 1 at 308), and to second means for calculating cardiac rate using a different, non-cycle driven analysis such as block data analysis at 322 which provides a second cardiac rate at 324 used by a correction means at 326 to correct the contents of the beat buffer at 306. Details of operation of a correction means are shown in FIGS. 8-9. FIG. 12 also shows an example with an input signal means 600 coupled to a first means for calculating cardiac rate at 610 and a second means for calculating cardiac rate at 620, with correction means at 650 coupled, via A, to the first cardiac rate calculation 610, for correcting data (such as a beat buffer generated with the first cardiac rate means 610). FIG. 13 shows another example with the signal input 700 providing data for first cardiac rate means 710 which generates a beat buffer 714 and second cardiac rate means 720, with the second cardiac rate means 720 providing information for a correction means 730 that is allowed to correct the beat buffer 714 when needed.

A sixth non-limiting example takes the form of a cardiac rhythm management device as in the fifth non-limiting example, wherein the correction means comprises interval means to determine a set of intervals between identified consecutive cardiac cycles of the beat buffer; an expected value generator for generating an expected value for an average of the intervals of the beat buffer using the second cardiac rate; and best fit means to determine a best fit of combinations of the set of intervals and identify which of the identified cardiac cycles should be eliminated such that an average interval for the beat buffer matches the expected value. FIG. 13 shows an example in which the correction means 730 operates via interval means 732, expected value means 734 and best fit means 736. FIGS. 8-9 show further details of such examples.

A seventh non-limiting example takes the form of a cardiac rhythm management device comprising signal means for receiving an cardiac electrical signal for analysis; a first means for calculating cardiac rate by identifying cardiac cycles within the cardiac electrical signal, to generate a first cardiac rate; a second means for calculating cardiac rate, without identifying cardiac cycles using the cardiac electrical signal, to generate a second cardiac rate; a decision means for determining, by analysis of the identified cardiac cycles, whether an arrhythmia is occurring; and bypass means for determining whether the second means is generating a persistent outcome and, if so, for bypassing the decision means to determine whether an arrhythmia is occurring directly from the second rate. FIG. 14 shows an example where a signal input means 800 provides information to a first cardiac rate calculation means 810 that relies on cardiac cycle detection 812, and to a second cardiac rate calculation means 820 that does not rely on cardiac cycle detection. A decision means is shown at 840, and a bypass means is shown at 860 for bypassing the decision means 840 as needed to generate a therapy command to block 846.

An eighth non-limiting example takes the form of a cardiac rhythm management device as in the seventh non-limiting example, wherein the bypass means is configured to determine that the second means is generating a persistent outcome by comparing a plurality of outputs of the second cardiac rate from the second means to one another and finding that the plurality of outputs are similar within predetermined conditions. As shown in FIG. 14, the bypass means 860 observes a persistent outcome in reliance on whether the rate 872 is repeatable. A detailed example for determining whether to trigger bypass means is also shown in FIG. 10.

A ninth non-limiting example takes the form of a cardiac rhythm management device as in the seventh non-limiting example wherein: the second means for calculating cardiac rate generates both the second cardiac rate and a confidence associated with the second cardiac rate in an iterative process for providing the second cardiac rate and associated confidence; and the bypass means is configured to determine that the second means is generating a persistent outcome by comparing a plurality of outputs of the second cardiac rate from the second means to one another and finding that the plurality of outputs are similar within predetermined conditions, and that confidences associated with the plurality of outputs are high. FIG. 4 provides details for a rate analysis that provides an output in terms of both rate and confidence, as further explained also in FIG. 6, where the block data analysis 272 provides a rate output 274 and confidence output 276. As shown in FIG. 14, the bypass means 860 may use both rate 872 and confidence 874 to determine whether a persistent outcome 870 occurs.

A tenth non-limiting example takes the form of a cardiac rhythm management device as in any of the seventh to ninth non-limiting examples further comprising therapy means for delivering a therapy to a patient, wherein the bypass means configured to determine whether the persistent outcome includes a second cardiac rate in a first range indicative of a treatable arrhythmia, and the bypass means is operable to bypass the decision means by activating the therapy means. FIG. 14 illustrates that the bypass means can reference a set of ranges for therapy, including those for anti-tachycardia pacing 882 and defibrillation 884, when determining whether to activate the therapy means 846.

An eleventh non-limiting example takes the form of a cardiac rhythm management device as in any of the seventh to tenth non-limiting examples wherein the bypass means is configured to determine whether the persistent outcome includes a second cardiac rate in a second range indicating that no treatable arrhythmia is occurring, and the bypass means is operable to bypass the decision means to prevent the decision means from activating the therapy means if the persistent outcome is in the second range. FIG. 14 shows that the bypass means 860 may reference a no-therapy rate range at 886 and determine to disable the therapy means or otherwise prevent operation of the decision, tracking and declaration means 840, 842, 844 to activate the therapy means.

A twelfth non-limiting example takes the form of a cardiac rhythm management device as in any of the seventh to ninth non-limiting examples further comprising therapy means for delivering a therapy to a patient, the therapy means being capable of delivering at least anti-tachycardia pacing and defibrillation therapy; wherein the bypass means is configured: if the persistent outcome includes a second cardiac rate in a first range indicating a condition treatable by defibrillation, to activate the therapy means for defibrillation therapy; if the persistent outcome includes a second cardiac rate in a second range indicating a condition treatable by anti-tachycardia pacing, to activate the therapy means for anti-tachycardia pacing therapy; and, if the persistent outcome includes a second cardiac rate below at least each of the first range and the second range, to prevent the decision means from activating the therapy means. FIG. 14 illustrates that the bypass means can reference a set of ranges for therapy, including those for anti-tachycardia pacing 882 and defibrillation 884, when determining whether to activate the therapy means 846, as well as a no-therapy range 886, if determining to disable the therapy means 846.

A thirteenth non-limiting example takes the form of a cardiac rhythm management device as in any of the first to twelfth non-limiting examples, wherein the second means for calculating cardiac rate is configured to analyze a block of cardiac electrical signal and determine a second cardiac rate, without identifying individual cardiac cycles, using a spectral analysis. The use of spectral analysis is noted in FIG. 12 at block 624 as a type of block analysis 622, which may also be used in any of the block analyses noted at FIG. 6, block 272, FIG. 7, block 322, FIG. 13, block 722, and FIG. 14, at 822.

A fourteenth non-limiting example takes the form of a cardiac rhythm management device as in any of the first to twelfth non-limiting examples, wherein the second means for calculating cardiac rate is configured to analyze a block of cardiac electrical signal and determine a second cardiac rate, without identifying individual cardiac cycles, by comparing the cardiac signal to itself in an iterative manner with time shifting to yield an autocorrelation. Such analysis is demonstrated in FIG. 4. Autocorrelation is noted at block 626 as a type of block analysis 622, which may also be used in any of the block analyses noted at FIG. 6, block 272, FIG. 7, block 322, FIG. 13, block 722, and FIG. 14, at 822.

A fifteenth non-limiting example takes the form of a cardiac rhythm management device as in any of the first to twelfth non-limiting examples, wherein the second means for calculating cardiac rate relies on one or more of heart sounds, pulse oximetry, cardiac motion, or blood pressure. FIG. 12 shows that the second cardiac rate means 620 may use an Other Signal 630 that may take the form of heart sounds 632, pulse oximetry data 634, cardiac motion data 636, and block pressure data 638, any of which may be used at block 724 in FIG. 13 and/or block 824 in FIG. 14.

A sixteenth non-limiting example takes the form of a cardiac rhythm management device as in any of the first to twelfth non-limiting examples, wherein the second means for calculating cardiac rate relies on communication with a second device to obtain a cardiac rate therefrom. FIG. 12 shows that the second cardiac rate means 620 may obtain a rate from a second device, as indicated at 640; likewise a second device can be used in FIG. 13 at 726 and FIG. 14 at 826.

A seventeenth non-limiting example takes the form of an implantable defibrillator system comprising a cardiac rhythm management device as in any of the first to sixteenth non-limiting examples. Use for therapy is noted in FIG. 12 at 670, FIG. 14 at 846, and an implantable defibrillator system is shown in FIG. 1.

An eighteenth non-limiting example takes the form of a wearable defibrillator system comprising a cardiac rhythm management device as in any of the first to sixteenth non-limiting examples. Use for therapy is noted in FIG. 12 at 670, FIG. 14 at 846, and use as an external defibrillator or wearable defibrillator is described variously above in reference to several figures including as an alternative to FIG. 1.

A nineteenth non-limiting example takes the form of a cardiac rhythm management device comprising a canister housing operational circuitry and having a port adapted for use with an implantable lead having a plurality of electrodes such that multiple sensing electrodes for sensing a cardiac electrical signal are available, with operational circuitry coupled to the port and configured to perform cardiac signal analysis comprising: receiving a cardiac electrical signal for analysis; calculating a first cardiac rate by identifying cardiac cycles in the cardiac electrical signal; calculating a second cardiac rate without identifying cardiac cycles; and determining, using the second cardiac rate, whether a set of detected cardiac cycles used for calculating the first cardiac rate comprises one or more overdetected cardiac cycles and, if so, correcting data related to the set of detected cardiac cycles.

A twentieth non-limiting example takes the form of a cardiac rhythm management device as in the nineteenth non-limiting example, wherein the operational circuitry is configured to calculate the first cardiac rate by: identifying cardiac cycles as detected events from within the cardiac electrical signal; certifying the detected events by identifying and omitting noise and correcting overdetection; and calculating an average of intervals between certified detected events and obtaining a rate therefrom; wherein the operational circuitry is configured to calculate the second cardiac rate iteratively at an interval using the cardiac electrical signal; and wherein the operational circuitry is configured to correct data related to the set of detected cardiac cycles by identifying a previously certified detected event as an overdetection.

A twenty-first non-limiting example takes the form of a cardiac rhythm management device as in the either of the nineteenth or twentieth non-limiting examples, wherein the operational circuitry is configured to perform morphology analysis to determine whether detected cardiac cycles match one or more templates, wherein the operational circuitry is configured to rely on outcomes from the morphology analysis to select which detected events, if any, are overdetection when correcting data related to the set of detected cardiac cycles.

A twenty-second non-limiting example takes the form of a cardiac rhythm management device as in any of the nineteenth to twenty-first non-limiting examples, wherein the operational circuitry is configured to calculate the second cardiac rate by comparing a block of the cardiac signal to itself in an iterative manner, with time shifting, to yield a number of comparison scores, and selecting a peak comparison score.

A twenty-third non-limiting example takes the form of a cardiac rhythm management device as in any of the nineteenth to twenty-first non-limiting examples, wherein the operational circuitry is configured to calculate the second cardiac rate by use of one or more of heart sounds, pulse oximetry, cardiac motion, or blood pressure.

A twenty-fourth non-limiting example takes the form of a cardiac rhythm management device as in any of the nineteenth to twenty-first non-limiting examples, wherein the operational circuitry is configured to calculate the second cardiac rate by communicating with a second device to obtain a cardiac rate therefrom.

A twenty-fifth non-limiting example takes the form of a cardiac rhythm management device comprising a canister housing operational circuitry and having a port adapted for use with an implantable lead having a plurality of electrodes such that multiple sensing electrodes for sensing a cardiac electrical signal are available, with operational circuitry coupled to the port and configured to perform cardiac signal analysis comprising: receiving a cardiac electrical signal for analysis; calculating a first cardiac rate by identifying cardiac cycles in the cardiac electrical signal; maintaining a beat buffer for tracking the identified cardiac cycles; calculating a second cardiac rate without identifying cardiac cycles; and correcting contents of the beat buffer in response to the second cardiac rate being different from the first cardiac rate.

A twenty-sixth non-limiting example takes the form of a cardiac rhythm management device as in the twenty-fifth non-limiting example, wherein the operational circuitry is further configured to: determine a set of intervals between identified consecutive cardiac cycles of the beat buffer; generate an expected value for an average of the intervals of the beat buffer using the second cardiac rate; and determine a best fit of combinations of the set of intervals and identify which of the identified cardiac cycles should be eliminated such that an average interval for the beat buffer matches the expected value.

A twenty-seventh non-limiting example takes the form of a cardiac rhythm management device as in the twenty-fifth non-limiting example, wherein the operational circuitry is configured to perform morphology analysis to determine whether detected cardiac cycles match one or more templates, wherein the operational circuitry is configured to rely on outcomes from the morphology analysis to correct contents of the beat buffer.

A twenty-eighth non-limiting example takes the form of a cardiac rhythm management device as in the twenty-fifth non-limiting example wherein the operational circuitry is configured to calculate the second cardiac rate by comparing a block of the cardiac signal to itself in an iterative manner, with time shifting, to yield a number of comparison scores, and selecting a peak comparison score. A twenty-ninth non-limiting example takes the form of a cardiac rhythm management device as in the twenty-fifth non-limiting example wherein the operational circuitry is configured to calculate the second cardiac rate by use of one or more of heart sounds, pulse oximetry, cardiac motion, or blood pressure. A thirtieth non-limiting example takes the form of a cardiac rhythm management device as in the twenty-fifth non-limiting example wherein the operational circuitry is configured to calculate the second cardiac rate by communicating with a second device to obtain a cardiac rate therefrom.

A thirty-first non-limiting example takes the form of a cardiac rhythm management device comprising a canister housing operational circuitry and having a port adapted for use with an implantable lead having a plurality of electrodes such that multiple sensing electrodes for sensing a cardiac electrical signal are available, with operational circuitry coupled to the port and configured to perform cardiac signal analysis comprising: receiving a cardiac electrical signal for analysis; calculating a first cardiac rate by identifying cardiac cycles in the cardiac electrical signal; determining, by analysis of the identified cardiac cycles and first cardiac rate, whether an arrhythmia is occurring to produce a first outcome; calculating a second cardiac rate without identifying cardiac cycles; and determining whether the second cardiac rate, over a series of measurements, provides a persistent outcome and, if so, bypassing the first outcome and determining whether an arrhythmia is occurring using the second rate and not the first rate.

A thirty-second non-limiting example takes the form of a cardiac rhythm management device as in the thirty-first non-limiting example wherein the operational circuitry is configured determine whether the second cardiac rate provides a persistent outcome by comparing a plurality of measurements of the second cardiac rate to one another and finding that the plurality of outputs are similar within predetermined conditions.

A thirty-third non-limiting example takes the form of a cardiac rhythm management device as in the thirty-first non-limiting example wherein: the operational circuitry is configured to calculate the second cardiac rate with a confidence score associated in an iterative process for providing a series of measurements of the second cardiac rate and associated confidence score for each measurement; and the operational circuitry is configured to determine whether the second cardiac rate provides a persistent outcome by comparing a plurality of measurements of the second cardiac rate to one another and finding that the plurality of measurements are similar within predetermined conditions, and that confidence scores associated with the plurality of measurements also exceed a threshold.

A thirty-fourth non-limiting example takes the form of a cardiac rhythm management device as in the thirty-first non-limiting example, wherein the operational circuitry includes therapy circuitry for delivering a therapy to a patient, and the operational circuitry is configured to bypass the first outcome and determine whether an arrhythmia is occurring using the second rate and not the first rate by determining whether the persistent outcome includes a second cardiac rate in a first range indicative of a treatable arrhythmia, and, if so, activating the therapy circuitry.

A thirty-fifth non-limiting example takes the form of a cardiac rhythm management device as in the thirty-fourth non-limiting example, wherein the operational circuitry is further configured to bypass the first outcome and determine whether an arrhythmia is occurring using the second rate and not the first rate by determining whether the persistent outcome includes a second cardiac rate in a second range indicating that no treatable arrhythmia is occurring, and, if so, preventing activation of the therapy circuitry.

A thirty-sixth non-limiting example takes the form of a cardiac rhythm management device as in the thirty-first non-limiting example wherein the operational circuitry includes therapy circuitry for delivering therapy to a patient, the therapy including at least anti-tachycardia pacing therapy and defibrillation therapy; wherein the operational circuitry is configured to bypass the first outcome and control the therapy circuitry as follows: if the persistent outcome includes a second cardiac rate in a first range indicating a condition treatable by defibrillation, activating the therapy circuitry for defibrillation therapy; if the persistent outcome includes a second cardiac rate in a second range indicating a condition treatable by anti-tachycardia pacing, activating the therapy circuitry for anti-tachycardia pacing therapy; and if the persistent outcome includes a second cardiac rate lower than at least the first range and the second range, preventing activation of the therapy circuitry.

A thirty-seventh non-limiting example takes the form of a cardiac rhythm management device as in the thirty-first non-limiting example wherein the operational circuitry is configured to calculate the second cardiac rate by comparing a block of the cardiac signal to itself in an iterative manner, with time shifting, to yield a number of comparison scores, and selecting a peak comparison score. A thirty-eighth non-limiting example takes the form of a cardiac rhythm management device as in the thirty-first non-limiting example wherein the operational circuitry is configured to calculate the second cardiac rate by use of one or more of heart sounds, pulse oximetry, cardiac motion, or blood pressure. A thirty-ninth non-limiting example takes the form of a cardiac rhythm management device as in the thirty-first non-limiting example wherein the operational circuitry is configured to calculate the second cardiac rate by communicating with a second device to obtain a cardiac rate therefrom.

A fortieth non-limiting example takes the form of an implantable defibrillator system comprising a cardiac rhythm management device as in any the nineteenth to thirty-ninth non-limiting examples. A forty-first non-limiting example takes the form of a wearable defibrillator system comprising a cardiac rhythm management device as in any the nineteenth to thirty-ninth non-limiting examples.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A cardiac rhythm management device comprising a canister housing operational circuitry and having a port adapted for use with an implantable lead having a plurality of electrodes such that multiple sensing electrodes for sensing a cardiac electrical signal are available, with operational circuitry coupled to the port and configured to perform cardiac signal analysis comprising:
   receiving a cardiac electrical signal for analysis;
   calculating a first cardiac rate by identifying cardiac cycles in the cardiac electrical signal;
   calculating a second cardiac rate without identifying cardiac cycles; and
   determining, using the second cardiac rate, whether a set of detected cardiac cycles used for calculating the first cardiac rate comprises one or more overdetected cardiac cycles and, if so, correcting data related to the set of detected cardiac cycles.

2. The cardiac rhythm management device of claim 1 wherein the operational circuitry is configured to calculate the first cardiac rate by:
   identifying cardiac cycles as detected events from within the cardiac electrical signal;
   certifying the detected events by identifying and omitting noise and correcting overdetection; and
   calculating an average of intervals between certified detected events and obtaining a rate therefrom;

wherein the operational circuitry is configured to calculate the second cardiac rate iteratively at an interval using the cardiac electrical signal; and wherein the operational circuitry is configured to correct data related to the set of detected cardiac cycles by identifying a previously certified detected event as an overdetection.

3. The cardiac rhythm management device of claim 1 wherein the operational circuitry is configured to perform morphology analysis to determine whether detected cardiac cycles match one or more templates, wherein the operational circuitry is configured to rely on outcomes from the morphology analysis to select which detected events, if any, are overdetection when correcting data related to the set of detected cardiac cycles.

4. The cardiac rhythm management device of claim 1 wherein the operational circuitry is configured to calculate the second cardiac rate by comparing a block of the cardiac signal to itself in an iterative manner, with time shifting, to yield a number of comparison scores, and selecting a peak comparison score.

5. The cardiac rhythm management device of claim 1 wherein the operational circuitry is configured to calculate the second cardiac rate by use of one or more of heart sounds, pulse oximetry, cardiac motion, or blood pressure.

6. The cardiac rhythm management device of claim 1 wherein the operational circuitry is configured to calculate the second cardiac rate by communicating with a second device to obtain a cardiac rate therefrom.

7. The cardiac rhythm management device of claim 1 wherein the operational circuitry is configured to maintain a beat buffer for tracking detected cardiac cycles as part of the cardiac signal analysis, further wherein the operational circuitry is configured to correct data related to the set of detected cardiac cycles by correcting contents of the beat buffer in response to the second cardiac rate being different from the first cardiac rate.

8. The cardiac rhythm management device of claim 7 wherein the operational circuitry is further configured to correct data related to the set of detected cardiac cycles by:
determining a set of intervals between identified consecutive cardiac cycles of the beat buffer;
generating an expected value for an average of the intervals of the beat buffer using the second cardiac rate; and
determining a best fit of combinations of the set of intervals and identify which of the identified cardiac cycles should be eliminated such that an average interval for the beat buffer matches the expected value.

9. A method of cardiac signal analysis performed by a cardiac rhythm management device including a canister housing operational circuitry and having a port adapted for use with an implantable lead having a plurality of electrodes such that multiple sensing electrodes for sensing a cardiac electrical signal are available, with the operational circuitry coupled to the port, the method comprising:
receiving a cardiac electrical signal for analysis from at least a pair of the sensing electrodes;
calculating a first cardiac rate by identifying cardiac cycles in the cardiac electrical signal;
calculating a second cardiac rate without identifying cardiac cycles;
determining, using the second cardiac rate, that a set of detected cardiac cycles used for calculating the first cardiac rate comprises one or more overdetected cardiac cycles, and, in response thereto,
correcting data related to the set of detected cardiac cycles.

10. The method of claim 9 in which the first cardiac rate is calculated by:
identifying cardiac cycles as detected events from within the cardiac electrical signal;
certifying the detected events by identifying and omitting noise and correcting overdetection; and
calculating an average of intervals between certified detected events and obtaining a rate therefrom;
wherein the second cardiac rate is calculated iteratively at an interval using the cardiac electrical signal; and
wherein the step of correcting data related to the set of detected cardiac cycles is performed by identifying a previously certified detected event as an overdetection.

11. The method of claim 9 further comprising the operational circuitry performing morphology analysis to determine whether detected cardiac cycles match one or more templates, wherein the step of correcting data related to the set of detected cardiac cycles is performed by using outcomes from the morphology analysis to select which detected events are overdetections.

12. The method of claim 9 wherein the second cardiac rate is calculated by the operational circuitry comparing a block of the cardiac signal to itself in an iterative manner, with time shifting, to yield a number of comparison scores, and selecting a peak comparison score.

13. The method of claim 9 wherein the second cardiac rate is calculated by the operational circuitry using one or more of heart sounds, pulse oximetry, cardiac motion, or blood pressure.

14. The method of claim 9 wherein the second cardiac rate is calculated by the operational circuitry communicating with a second device to obtain a cardiac rate therefrom.

15. The method of claim 9 further comprising maintaining a beat buffer for tracking detected cardiac cycles as part of the cardiac signal analysis, further wherein the step of correcting data related to the set of detected cardiac cycles is performed by correcting contents of the beat buffer in response to the second cardiac rate being different from the first cardiac rate.

16. The method of claim 15 wherein the contents of the beat buffer are corrected by:
determining a set of intervals between identified consecutive cardiac cycles of the beat buffer;
generating an expected value for an average of the intervals of the beat buffer using the second cardiac rate; and
determining a best fit of combinations of the set of intervals and identify which of the identified cardiac cycles should be eliminated such that an average interval for the beat buffer matches the expected value.

* * * * *